United States Patent
Fukazawa

(10) Patent No.: US 10,274,835 B2
(45) Date of Patent: Apr. 30, 2019

(54) EVALUATION METHOD AND DEVICE, PROCESSING METHOD, AND EXPOSURE SYSTEM

(71) Applicant: NIKON CORPORATION, Tokyo (JP)

(72) Inventor: Kazuhiko Fukazawa, Kamakura (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 14/654,394

(22) PCT Filed: Dec. 20, 2013

(86) PCT No.: PCT/JP2013/084258
§ 371 (c)(1),
(2) Date: Jun. 19, 2015

(87) PCT Pub. No.: WO2014/098220
PCT Pub. Date: Jun. 26, 2014

(65) Prior Publication Data
US 2015/0338745 A1 Nov. 26, 2015

(30) Foreign Application Priority Data
Dec. 20, 2012 (JP) .................................. 2012-278753

(51) Int. Cl.
G03B 27/32 (2006.01)
G03F 7/20 (2006.01)
(Continued)

(52) U.S. Cl.
CPC ..... *G03F 7/70616* (2013.01); *G01N 21/8806* (2013.01); *G01N 21/8851* (2013.01);
(Continued)

(58) Field of Classification Search
CPC .. G03F 7/70058; G03F 7/705; G03F 7/70516; G03F 7/7055; G03F 7/70558;
(Continued)

(56) References Cited

U.S. PATENT DOCUMENTS 6,594,012 B2 7/2003 Takeuchi et al.
9,240,356 B2 1/2016 Fukazawa et al.
(Continued)

FOREIGN PATENT DOCUMENTS

JP 10-22205 1/1998
JP 2007-335610 12/2007
(Continued)

OTHER PUBLICATIONS

Written Opinion of the International Searching Authority of International Application No. PCT/JP2013/084258 dated Mar. 25, 2014.
(Continued)

*Primary Examiner* — Christina A Riddle
(74) *Attorney, Agent, or Firm* — Finnegan, Henderson, Farabow, Garrett & Dunner, LLP

(57) ABSTRACT

Using a substrate on which a structure has been formed with a plurality of sets of processing conditions, the present disclosure provides an evaluation device that evaluates one of said sets of processing conditions with high precision. This evaluation device is provided with an illumination system that uses illuminating light to illuminate a wafer on which a pattern has been provided via exposure using a plurality of sets of exposure conditions, including first exposure conditions and second exposure conditions; a light-receiving system and an imaging unit the detect light coming from the surface of the wafer; and a computation unit that, on the basis of detection results obtained by the imaging unit using first diffraction conditions and second diffraction conditions that differ in terms of illumination conditions and/or detection conditions, and that estimates the first exposure conditions used when the wafer is exposed.

21 Claims, 22 Drawing Sheets

(51) Int. Cl.
*G01N 21/88* (2006.01)
*G01N 21/95* (2006.01)
(52) U.S. Cl.
CPC ......... *G01N 21/9501* (2013.01); *G03F 7/705* (2013.01); *G03F 7/70058* (2013.01); *G03F 7/70558* (2013.01); *G03F 7/70625* (2013.01); *G03F 7/70641* (2013.01); *G01N 2021/8848* (2013.01)
(58) Field of Classification Search
CPC ............ G03F 7/70616; G03F 7/70625; G03F 7/70641; G03F 7/70666; G03F 7/70675; G03F 7/70683; G03F 7/70991; G01N 21/8806; G01N 21/8851; G01N 21/9501; G01N 2021/8848
USPC ......... 355/52, 53, 55, 67–75, 77; 250/492.1, 250/492.2, 492.22, 493.1, 548; 356/364–370, 601–609, 625, 634, 635, 356/636
See application file for complete search history.

(56) References Cited

U.S. PATENT DOCUMENTS

| | | | |
|---|---|---|---|
| 2002/0054290 A1* | 5/2002 | Vurens | G01J 4/04 356/369 |
| 2002/0100012 A1 | 7/2002 | Sutanl et al. | |
| 2004/0063232 A1* | 4/2004 | Komatsu | H01L 21/67288 438/18 |
| 2004/0190008 A1* | 9/2004 | Mieher | G01N 21/956 356/625 |
| 2005/0116187 A1* | 6/2005 | Uda | G01N 21/956 250/559.45 |
| 2007/0242247 A1 | 10/2007 | Shiraishi | |
| 2008/0137052 A1* | 6/2008 | Matsumoto | G03B 27/52 355/62 |
| 2009/0103080 A1* | 4/2009 | Oomori | G01B 11/14 356/237.5 |
| 2011/0235038 A1* | 9/2011 | Fukazawa | G01N 21/21 356/369 |
| 2012/0099120 A1 | 4/2012 | Okamoto | |
| 2013/0070244 A1 | 3/2013 | Fukazawa et al. | |
| 2013/0217154 A1 | 8/2013 | Fukazawa et al. | |

FOREIGN PATENT DOCUMENTS

| | | |
|---|---|---|
| JP | 2008-147258 | 6/2008 |
| KR | 10-2008-0052397 | 6/2008 |
| TW | 201022663 A1 | 6/2010 |
| WO | WO 2011/001678 A1 | 1/2011 |
| WO | WO 2012/056601 A1 | 5/2012 |

OTHER PUBLICATIONS

Notification of Reasons for Refusal from the Japanese Patent Office, in counterpart Japanese Patent Application No. 2014-553218, dated Jan. 26, 2016.

International Search Report issued by the Japanese Patent Office in International Application No. PCT/JP2013/084258, dated Mar. 25, 2014 (5 pages).

The Notice of Preliminary Rejection issued by the Korean Intellectual Property Office of Korean Patent Application No. 10-2015-7019500, dated Sep. 28, 2016 and its translation (11 pages total).

Office Action issued by the Taiwan Intellectual Property Office in a counterpart Application No. 102147415 dated Mar. 24, 2017, and English translation thereof.

Taiwanese Office Action dated Oct. 11, 2018 by the Taiwanese Patent Office in corresponding Taiwanese Patent Application No. 107100402.

\* cited by examiner

SPACER DEPOSITING AMOUNT ts

ETCHING AMOUNT te

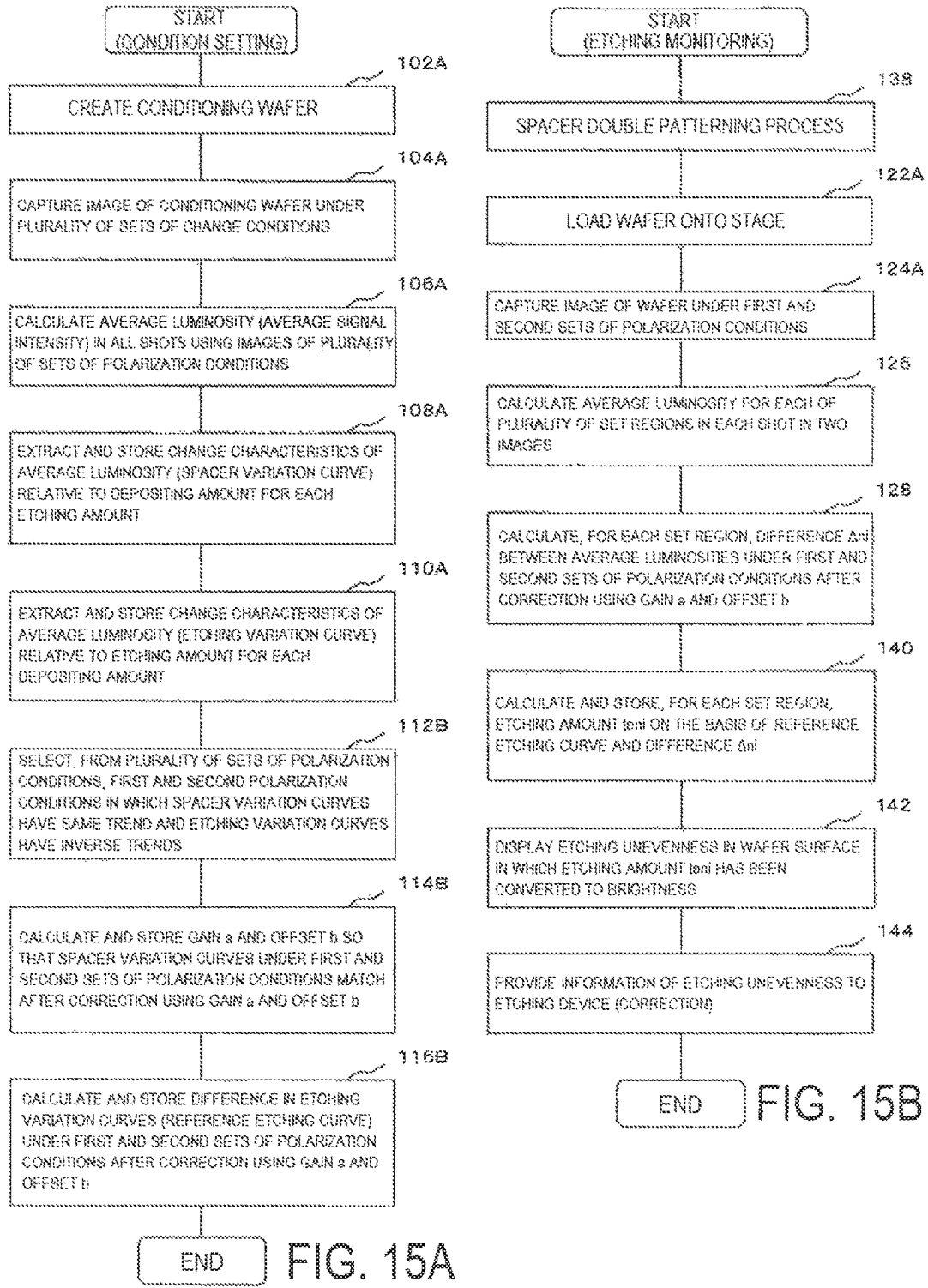

EVALUATION METHOD AND DEVICE, PROCESSING METHOD, AND EXPOSURE SYSTEM

TECHNICAL FIELD

The present disclosure relates to techniques for evaluating a substrate having a structure provided through processing under a plurality of processing conditions, and to processing techniques and exposure techniques that use such evaluation techniques, and to techniques for manufacturing devices using such processing techniques.

BACKGROUND ART

In exposure devices such as scanning steppers or steppers used in lithography processes for manufacturing semiconductor devices and the like, it is necessary to manage a plurality of sets of exposure conditions such as a dose quantity (an exposure quantity), a focal position (a defocus amount for the substrate to be exposed relative to an image plane of a projection optical system), an exposure wavelength, and the like with high precision. To do so, it is necessary to expose a substrate using an exposure device and evaluate the actual exposure conditions of the exposure device with high precision using a pattern or the like formed on the exposed substrate.

As a conventional method for evaluating a focal position in an exposure device, for example, a pattern for evaluation in a reticle is illuminated by illumination light whose principle ray is tilted. A substrate is exposed with an image of the pattern at a plurality of shots while varying the height of the substrate in sequence by a stage. A horizontal shift amount of a resist pattern obtained through post-exposure development is measured, and the focal position during the exposure of each shot is then evaluated on the basis of the measurement results (see Patent Literature 1, for example).

CITATION LIST

Patent Literature

Patent Literature 1: US Patent Application Publication No. 2002/0100012.
Patent Literature 2: US Patent Application Publication No. 2007/242247.

SUMMARY OF EMBODIMENTS

Technical Problem

In the conventional focal position evaluation method, there is a risk that the measurement results will be affected to a certain degree by variations in dose quantities and the like. To more precisely evaluate individual exposure conditions, it is preferable to suppress the influence of other exposure conditions to the greatest extent possible.

Meanwhile, the conventional focal position evaluation method requires that a dedicated evaluation pattern be exposed, and evaluation has thus been difficult in cases where patterns of actual devices are exposed.

In light of such problems, to the present disclosure discloses, using a substrate on which a structure has been formed with a plurality of processing conditions (exposure conditions, for example), to evaluate one of the sets of processing conditions with high precision.

Solution to Problem

A first aspect consistent with the present disclosure provides an evaluation device including: an illumination unit that illuminates, with illumination light, a substrate on which a structure has been formed with a plurality of sets of processing conditions including first and second sets of processing conditions; a detection unit that detects light coming from a processed surface of the substrate due to the illumination light; and an estimating unit that estimates at least one of the first set of processing conditions and the second set of processing conditions, upon processing the substrate, on the basis of a detection result obtained by the detection unit under a plurality of sets of evaluation conditions among which at least one of illumination conditions of the illumination unit and detection conditions of the detection unit differ.

In addition, a second aspect provides an exposure system including an exposure unit having a projection optical system that exposes a surface of a substrate with a pattern, and the evaluation device according to the first aspect; here, processing conditions in the exposure unit are corrected on the basis of the first set of processing conditions estimated by the estimating unit of the evaluation device.

In addition, a third aspect provides an evaluation method including the steps of: illuminating, with illumination light, a substrate on which a structure has been formed with a plurality of sets of processing conditions including first and second sets of processing conditions; detecting light coming from a processed surface of the substrate due to the illumination light; and estimating at least one of the first set of processing conditions and the second set of processing conditions, upon processing the substrate, on the basis of a detection result obtained by detecting the light coming from the processed surface under a plurality of sets of evaluation conditions among which at least one of illumination conditions of the illumination light and detection conditions for the light coming from the processed surface differ.

In addition, a fourth aspect provides a processing method including the steps of: providing a pattern by processing a surface of a substrate; estimating the first set of processing conditions of the substrate using the evaluation method according to the third aspect; and correcting processing conditions used when exposing the substrate on the basis of the first set of processing conditions estimated in the evaluation method.

In addition, a fifth aspect provides a device manufacturing method including a step of processing that provides a pattern in a surface of a substrate, the processing method according to the fourth aspect being used in the step of processing.

In addition, a sixth aspect provides a device manufacturing method including a step of processing that provides a pattern in a surface of a substrate, the processing method according to the fourth aspect being used in the step of processing, and an arithmetic expression applied in order to suppress an amount of change relative to a change in the second set of processing conditions being stored in accordance with the device to be manufactured.

Exemplary Effects of Embodiments

Consistent with the present disclosure, by using a substrate on which a structure has been formed using a plurality of sets of processing conditions, one of the sets of processing conditions can be evaluated with high precision.

BRIEF DESCRIPTION OF DRAWINGS

FIG. 15A is a flowchart illustrating an example of condition setting according to a second embodiment, and FIG. 15B is a flowchart illustrating a method for evaluating etching according to the second embodiment.

DESCRIPTION OF EMBODIMENTS

[First Embodiment]

Figure 1A:
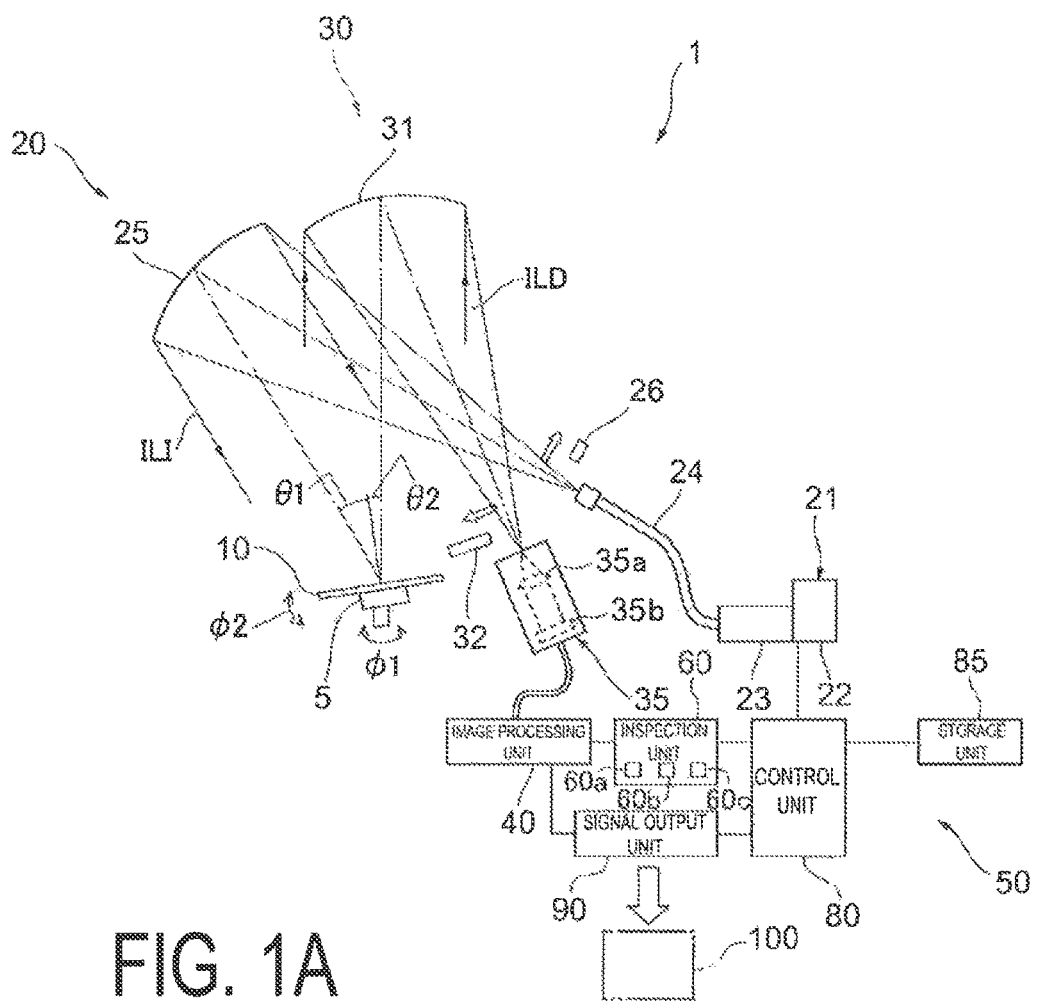
FIG. 1A is a diagram illustrating the overall configuration of an evaluation device according to an embodiment.
Figure 1B:
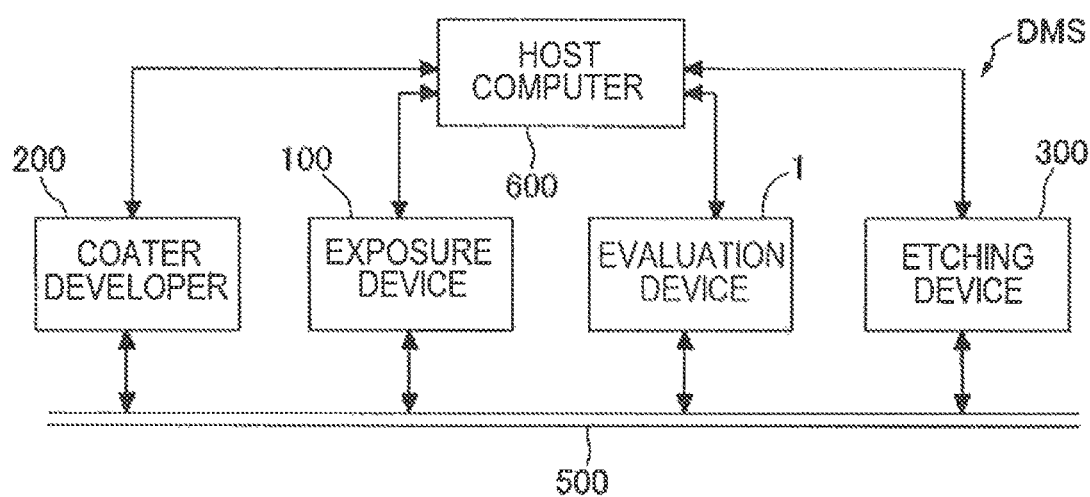
FIG. 1B is a block diagram illustrating a device manufacturing system.

Hereinafter, a first embodiment consistent with the present disclosure will be described with reference to FIGS. 1 to 11. FIG. 1A illustrates an evaluation device 1 according to the present embodiment, and FIG. 1B illustrates a device manufacturing system DMS according to the present embodiment. In FIG. 1B, the device manufacturing system DMS includes a thin-film forming device (not illustrated) that forms a thin film on a surface (wafer surface) of a semiconductor wafer (called simply a "wafer" hereinafter) serving as a semiconductor substrate, a coater developer 200 that coats the wafer surface with a resist (a photosensitive material) and develops the resist, an exposure device 100 that exposes the wafer surface coated with the resist with a circuit pattern for a semiconductor device or the like, and the evaluation device 1 that evaluates exposure conditions in the exposure device 100 as processing conditions using a structure formed on the wafer surface after the exposure and development. A liquid immersion-type scanning stepper (scanning-type projection exposure device) such as that disclosed in Patent Literature 2, which is incorporated herein by reference, is used as the exposure device 100, for example. The device manufacturing system DMS further includes an etching device that processes the developed wafer, a transport system 500 that transports the wafer between these devices, and a host computer 600 that exchanges control information and the like among these devices.

In FIG. 1A, the evaluation device 1 includes a stage 5 that supports a substantially disk-shaped wafer 10, and the wafer 10 transported by the transport system 500 illustrated in FIG. 1B is placed upon a top surface of the stage 5 (a placement surface) and is fixed and held through vacuum suction, for example. The stage 5 is supported on a base member (not illustrated) through a first driving unit (not illustrated) that controls an angle $\varphi 1$ that takes a center axis of the stage 5 as an axis of rotation, and a second driving unit (not illustrated) that controls a tilt angle $\varphi 2$ (a tilt angle of the surface of the wafer 10), which is an angle of tilt that, for example, passes through a top surface of the stage 5 and takes an axis perpendicular to the depiction in FIG. 1A as an axis of rotation.

The evaluation device 1 further includes an illumination system 20 that illuminates the surface of the wafer 10 supported on the stage 5 (the wafer surface) with illumination light ILI as collimated light, a light-receiving system 30 that condenses light emitted from the wafer surface under the illumination of the illumination light ILI (reflected light beams, diffracted light beams, or the like), an image capturing device 35 that detects an image of the wafer surface by receiving the light condensed by the light-receiving system 30, and a computation unit 50 that processes image signals and the like outputted from the image capturing device 35. The image capturing device 35 has an image forming lens 35a that forms an image of the wafer surface and a two-dimensional image capturing element 35b such as a CCD or a CMOS, and the image capturing element 35b captures an image of the entire surface of the wafer 10 at once and outputs an image signal. The computation unit 50 includes an image processing unit 40 that generates information of a digital image of the wafer 10 (a luminosity for each of pixels, an average luminosity for each shot, an average luminosity for each of regions smaller than a shot, or the like) on the basis of the image signal of the wafer 10 inputted from the image capturing device 35, an inspection unit 60 having computation units 60a, 60b, and 60c that process the image information outputted from the image processing unit 40, a control unit 80 that controls operations and the like of the image processing unit 40 and the inspection unit 60, a storage unit 85 that stores information regarding images and the like, and a signal output unit 90 that outputs obtained exposure conditions evaluation results to a control unit (not illustrated) in the exposure device 100 via the host computer 600. Note that the computation unit 50 may be constituted by a computer as a whole, and the inspection unit 60, the control unit 80, and the like may be functions implemented as computer software.

The illumination system 20 has an illuminating unit 21 that emits illumination light and an illumination-side concave mirror 25 that reflects the illumination light emitted from the illuminating unit 21 toward the wafer surface as collimated light. The illuminating unit 21 has a light source unit 22 such as a metal halide lamp or a mercury lamp, a light control unit 23 that, in response to a command from the control unit 80, selects light of a predetermined wavelength (a wavelength λ1, λ2, λ3, or the like, for example) from light from the light source unit 22 and adjusts an intensity thereof, and an optical guide fiber 24 that emits light selected and whose intensity has been adjusted by the light control unit 23 toward the illumination-side concave mirror 25 from a predetermined emission point. As one example, the wavelength λ1 is 248 nm, λ2 is 265 nm, and λ3 is 313 nm. In this case, the emission end of the optical guide fiber 24 is disposed at a focal surface of the illumination-side concave mirror 25, and thus the illumination light ILI reflected by the illumination-side concave mirror 25 irradiates the wafer surface as a collimated light flux. An angle of incidence θ1 of the illumination light on the wafer 10 can be adjusted by controlling the tilt angle φ2 of the stage 5 in response to a command from the control unit 80.

Figure 2A:
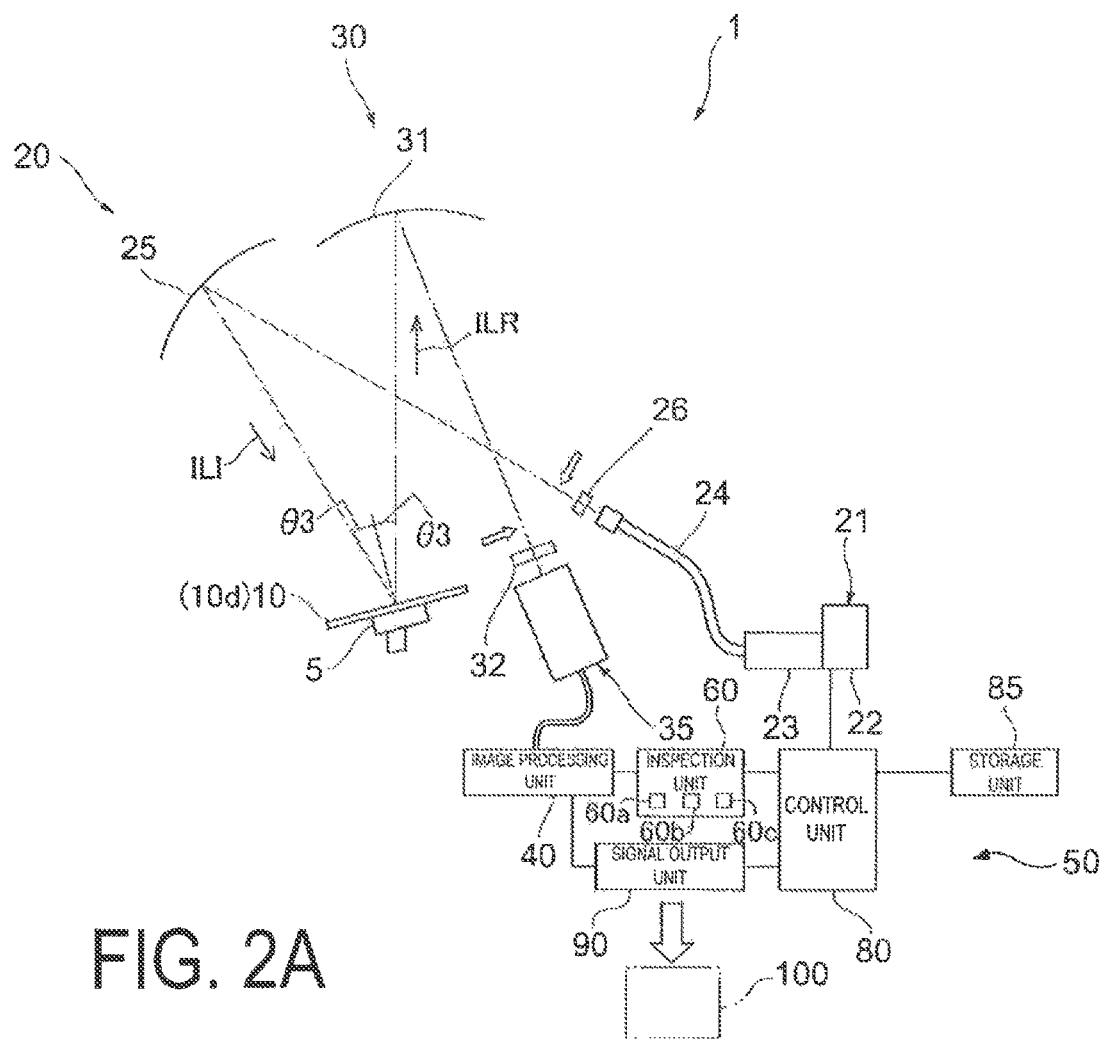
FIG. 2A is a diagram illustrating an evaluation device in which a polarizing filter is inserted into an optical path.

Meanwhile, an illumination-side polarizing filter 26 is provided between the optical guide fiber 24 and the illumination-side concave mirror 25 so as to be capable of being inserted into and retracted from an optical path by a driving unit (not illustrated) on the basis of a command from the control unit 80. As illustrated in FIG. 1A, inspection using diffracted light beams ILD from the wafer 10 (called "diffraction inspection" hereinafter for the sake of simplicity) is carried out while the illumination-side polarizing filter 26 is retracted from the optical path. On the other hand, as illustrated in FIG. 2A, inspection using polarized light (changes in a polarization state due to structural birefringence) (called "PER inspection" hereinafter for the sake of simplicity) is carried out while the illumination-side polarizing filter 26 is inserted into the optical path. The illumination-side polarizing filter 26 is a linearly polarizing plate capable of controlling an angle of rotation, for example. Note that it is also possible to disposed the illumination-side polarizing filter 26 in the optical path even during diffraction inspection, so that the illumination light ILI becomes S-polarized light relative to the wafer 10 (that is, linearly polarized light in a direction perpendicular to the incidence surface). With diffraction inspection using S-polarized light, the state of an uppermost layer of the wafer 10 can be detected with little influence from an underlying layer.

The light-receiving system 30 has a light receiving-side concave mirror 31 disposed facing the stage 5 (the wafer 10), and a light-incident portion of the image capturing device 35 is disposed at a focal surface of the light receiving-side concave mirror 31. Accordingly, the collimated light coming from the wafer surface is condensed on the image capturing device 35 by the light receiving-side concave mirror 31, and an image of the wafer 10 is formed on an image forming surface of the image capturing element 35b in the image capturing device 35.

Meanwhile, a light receiving-side polarizing filter 32 is provided between the light receiving-side concave mirror 31 and the image capturing device 35 so as to be capable of being inserted into and retracted from an optical path by a driving unit (not illustrated) on the basis of a command from the control unit 80. As illustrated in FIG. 1A, the diffraction inspection is carried out while the light receiving-side polarizing filter 32 is retracted from the optical path. On the other hand, as illustrated in FIG. 2A, the PER inspection is carried out while the light receiving-side polarizing filter 32 is inserted into the optical path. Like the illumination-side polarizing filter 26, the light receiving-side polarizing filter 32 is a linearly polarizing plate capable of controlling an angle of rotation, for example. During PER inspection, a polarization direction of the light receiving-side polarizing filter 32 is normally set to a crossed nicols state orthogonal to the polarization direction of the illumination-side polarizing filter 26.

As its most basic operation, the inspection unit 60 inspects whether or not defects (abnormalities) are present in the wafer surface by comparing the digital image of the wafer 10 supplied from the image processing unit 40 with image data of a non-defective wafer stored in the storage unit 85, in response to a command from the control unit 80. A result of the inspection performed by the inspection unit 60 and an image of that wafer surface are then outputted to and displayed in an image display device (not illustrated). In the present embodiment, the inspection unit 60 processes the image of the wafer surface as described later, and evaluates predetermined exposure conditions among a plurality of sets of exposure conditions, such as a dose quantity at which the exposure device 100 has exposed the wafer 10 (an exposure quantity or an exposure energy), a focal position (a position of an exposed surface in an optical axis direction of a projection optical system), an exposure wavelength (a central wavelength and/or a half width), a temperature of a liquid between the projection optical system and the wafer when exposing using an immersion method, and the like. A result of evaluating the exposure conditions is supplied to a control unit (not illustrated) in the exposure device 100, and the exposure device 100 can correct the exposure conditions (correct offset, variations, and the like, for example) on the basis of the evaluation result.

Figure 2B:
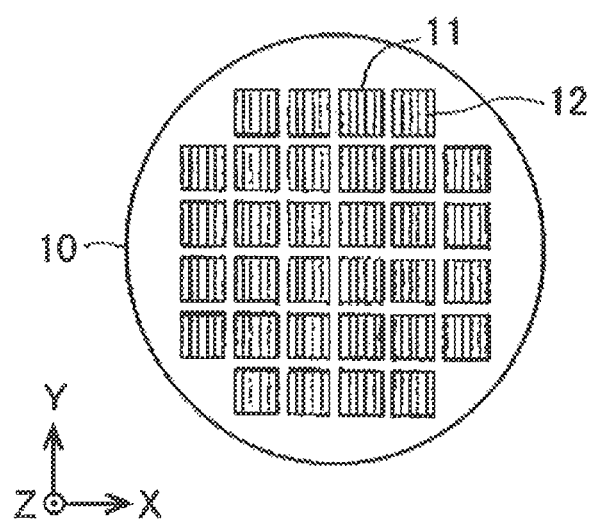
FIG. 2B is a plan view illustrating an example of a pattern on a surface of a semiconductor wafer.

Meanwhile, the exposure device 100 projects a predetermined pattern onto a resist in the uppermost layer of the wafer 10 and exposes the resist, and after development by the coater developer 200, the wafer 10 is transported into the stage 5 of the evaluation device 1 by the transport system 500. At this time, the wafer 10 is transported onto the stage 5 having undergone alignment by an alignment mechanism (not illustrated) during the transport process, using a pattern within the shots on the wafer 10, a mark on the wafer surface (a search-alignment mark, for example), or an outer edge portion (a notch, an orientation flat, or the like, for example) as a reference. As illustrated in FIG. 2B, a plurality of shots (shot regions) 11 are arranged on the wafer surface at predetermined intervals in two orthogonal directions (assumed here to be a X direction and a Y direction), and a non-planar repeating pattern 12, such as a line pattern, a hole pattern, or the like, is formed in each shot 11 as a semiconductor device circuit pattern. Note that an axis perpendicular to an XY plane is taken as a Z axis. The repeating pattern 12 may be a resist pattern, for example. Although a plurality of chip regions are often included in a single shot 11, it should be noted that FIG. 2B illustrates a single chip region in a single shot in order to facilitate understanding.

To carry out diffraction inspection of the wafer surface (inspection carried out by detecting the diffracted light beams ILD from the wafer 10) using the evaluation device 1 configured as described above, the control unit 80 loads recipe information (inspection conditions, procedures, and the like) stored in the storage unit 85 and carries out the following processing. First, as illustrated in FIG. 1A, the illumination-side polarizing filter 26 and the light receiving-side polarizing filter 32 are retracted from the optical path and the wafer 10 is transported onto the stage 5 by the transport system 500. Note that the wafer 10 is placed on the stage 5 at a predetermined position and in a predetermined direction on the basis of position information of the wafer 10 obtained by the alignment mechanism (not illustrated) during the transport.

Next, the angle φ1 of the stage 5 is adjusted so that a direction of the incidence surface of the illumination light ILI on the wafer surface (an illumination direction) matches the cycle direction (or repetition direction) of the repeating pattern 12 in each shot 11 (is orthogonal to the lines, in the case of a line pattern). When a pitch of the repeating pattern 12 is represented by P, a wavelength of the illumination light ILI incident on the wafer 10 is represented by λ, the angle of incidence of the illumination light ILI is represented by θ1, and a diffraction angle of the n-order (where n is an integer aside from 0) diffracted light beams ILD from the wafer surface that are to be detected is represented by θ2, the tilt angle φ2 of the stage 5 is adjusted so that the following formula (Formula 1) holds true.

$$P = n \times \lambda / \{\sin(\theta 1) - \sin(\theta 2)\} \quad \text{[Formula 1]}$$

Next, the illumination light ILI begins to be emitted from the illuminating unit 21 at a predetermined selected wavelength. As a result, the illumination light ILI emitted from the optical guide fiber 24 is reflected by the illumination-side concave mirror 25 and turns into collimated light with which the wafer surface is then irradiated. The diffracted light beams ILD diffracted by the wafer surface are condensed on the image capturing device 35 by the light receiving-side concave mirror 31, and an image (diffraction image) of the entire surface of the wafer 10 is formed on the image forming surface of the image capturing device 35. The image capturing device 35 outputs an image signal of that image to the image processing unit 40, the image processing unit 40 generates a digital image of the wafer surface, and information of that image is outputted to the inspection unit 60. In this case, the image of the wafer surface is formed on the image forming surface by the diffracted light beams ILD as a result of the conditions of the aforementioned formula (Formula 1) being met.

A combination of the wavelength λ of the illumination light ILI and the tilt angle φ2 of the stage 5 (the angle of incidence θ1 or the diffraction angle θ2), when the levels of individual image signals of the digital image obtained from the wafer surface (image luminosities at corresponding areas) are on average greater than or equal to a given intensity (luminosity), is called a single set of diffraction conditions. The aforementioned recipe information contains a plurality of sets of diffraction conditions. In some embodiments, the tilt angle φ2 of the stage 5 may be adjusted so that the image luminosities at areas corresponding to the obtained digital image are on average greater than or equal to a given luminosity. This method for adjusting the tilt angle φ2 can also be called diffraction condition searching.

Figure 3A:
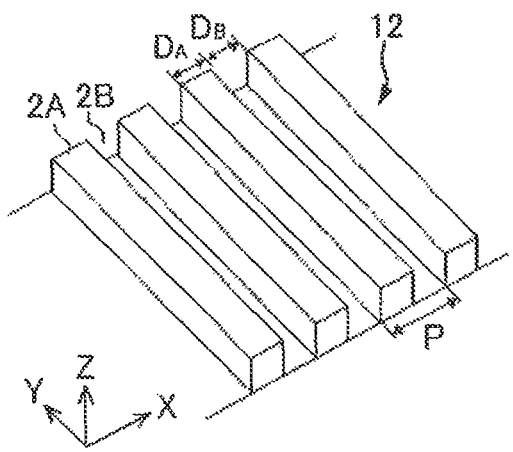
FIG. 3A is an enlarged perspective view illustrating a non-planar structure having a repeating pattern.

Next, PER inspection (inspection based on changes in the polarization state of reflected light beams) of the wafer surface by the evaluation device 1 will be described. In this case, it is assumed that the repeating pattern 12 in the wafer surface illustrated in FIG. 2B is a resist pattern (line pattern) in which a plurality of line portions 2A are arranged, along an arrangement direction (the X direction, here) that corresponds to a short-side direction of the line portions 2A, at a constant pitch (cycle) P with space portions 2B interposed therebetween, as illustrated in FIG. 3A. The arrangement direction of the line portions 2A (the X direction) is also called the cycle direction (or repetition direction) of the repeating pattern 12.

Here, a design value of a line width $D_A$ of the line portions 2A in the repeating pattern 12 is assumed to be ½ the pitch P. In the case where the repeating pattern 12 is formed according to the design value, the line width $D_A$ of the line portions 2A and a line width $D_B$ of the space portions 2B are equal, and a volume ratio between the line portions 2A and the space portions 2B is substantially 1:1. As opposed to this, if the focal position of the exposure device 100 departs from a best focal position (a correct value) when the repeating pattern 12 is formed, the pitch P will remain the same but the line widths $D_A$ and $D_B$ of the line portions 2A and the space portions 2B will differ from the design value, causing the volume ratio between the line portions 2A and the space portions 2B to depart from substantially 1:1.

The PER inspection inspects the state (whether fair or poor and the like) of the repeating pattern 12 using changes in the polarization state of the reflected light beams caused by changes in the volume ratio between the line portions 2A and the space portions 2B in the repeating pattern 12 as described above. To simplify the descriptions, an ideal volume ratio (design value) is assumed to be 1:1. Changes in the volume ratio are caused by shifts from a correct value of the focal position and the like, and appear in each shot 11 of the wafer 10 and furthermore in a plurality of regions within a shot 11. Note that volume ratio can also be rephrased as a cross-sectional shape area ratio.

Figure 3B:
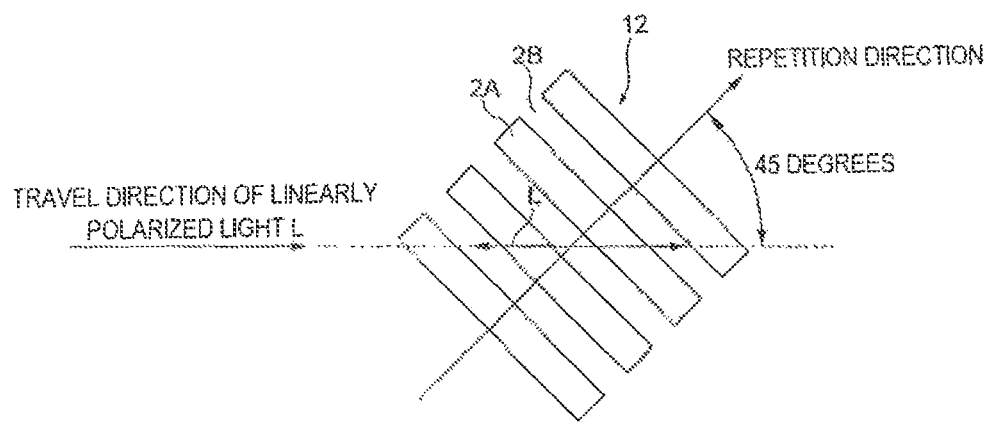
FIG. 3B is a diagram illustrating a relationship between a linearly polarized light incidence surface and a cycle direction (or repetition direction) of the repeating pattern.

To carry out PER inspection of the wafer surface using the evaluation device 1 according to the present embodiment, the control unit 80 loads recipe information (inspection conditions, procedures, and the like) stored in the storage unit 85 and carries out the following processing. First, as illustrated in FIG. 2A, the illumination-side polarizing filter 26 and the light receiving-side polarizing filter 32 are inserted into the optical path. Then, the wafer 10 is transported onto the stage 5 by the transport system 500 illustrated in FIG. 1B. Note that the wafer 10 is placed on the stage 5 at a predetermined position and in a predetermined direction on the basis of position information of the wafer 10 obtained by the alignment mechanism (not illustrated) during the transport. Meanwhile, when carrying out PER inspection, the tilt angle of the stage 5 is set so that the light-receiving system 30 can receive directly-reflected light beams ILR from the wafer 10, or in other words, so that an angle of reflection of the light received by the light-receiving system 30 relative to the wafer surface is equal to an angle of incidence of the incident illumination light ILI (an angle θ3 illustrated in FIG. 2A). Furthermore, an angle of rotation of the stage 5 is set so that the cycle direction of the repeating pattern 12 in the wafer surface is, as illustrated in FIG. 3B, tilted by 45 degrees relative to a vibration direction of the illumination light at the wafer surface (P-polarized linearly polarized light L, in FIG. 3B). This is to obtain the highest signal intensity of the reflected light beams from the repeating pattern 12. Meanwhile, in the case where an angle between the cycle direction and the stated vibration direction is set to 22.5 degrees or 67.5 degrees is order to increase the sensitivity of detection (a ratio of a change in a detection signal relative to a change in the exposure conditions), the angle may be changed. The angle is not limited these values, and can be set to any desired angle.

The illumination-side polarizing filter 26 is disposed between the optical guide fiber 24 and the illumination-side concave mirror 25 with the passage axis thereof set to a predetermined orientation (direction), and extracts (transmits) a polarized component (linearly polarized light) from the light from the illuminating unit 21 on the basis of the passage axis. As one example, in the present embodiment, the light emitted from the optical guide fiber 24 becomes P-polarized linearly polarized light L (see FIG. 3B) via the illumination-side polarizing filter 26 and the illumination-side concave mirror 25, with which the wafer surface is then irradiated.

At this time, the illumination light ILI incident on the wafer surface (the linearly polarized light L, here) is P-polarized light, and thus as illustrated in FIG. 3B, in the case where the cycle direction of the repeating pattern 12 is set to a 45-degree angle relative to the incidence surface of the light L (a travel direction of the light L on the wafer surface), the angle formed between the vibration direction of the light L on the wafer surface and the cycle direction of the repeating pattern 12 is also set to 45 degrees. To rephrase, the linearly polarized light L is incident on the repeating pattern 12 crossways at an angle in a state where the vibration direction of the light L on the wafer surface is tilted by 45 degrees relative to the cycle direction of the repeating pattern 12.

The collimated directly-reflected light beams ILR reflected by the wafer surface are condensed by the light receiving-side concave mirror 31 of the light-receiving system 30 and strike the image forming surface of the image capturing device 35 via the light receiving-side polarizing filter 32. At this time, the polarization state of the directly-reflected light beams ILR (the linearly polarized light L, here) changes to elliptical polarized light, for example, due to structural birefringence at the repeating pattern 12. The orientation of a passage axis of the light receiving-side polarizing filter 32 is set to be orthogonal (in a crossed nicols state) relative to the passage axis of the aforementioned illumination-side polarizing filter 26. Accordingly, the light receiving-side polarizing filter 32, a polarized component whose vibration direction is at substantially a right angle to the light L of the directly-reflected light beams from the wafer 10 (the repeating pattern 12) is extracted and conducted to the image capturing device 35. As a result, an image of the wafer surface is formed on the image forming surface of the image capturing device 35 by a polarized component whose vibration direction is at substantially a right angle to the light L of the directly-reflected light beams from the wafer 10 (an S-polarized component, when the light L is P-polarized light). Note that in the case where a minor axis direction of the elliptical polarized light is not orthogonal to the polarization direction of the light L, the passage axis of the light receiving-side polarizing filter 32 may be aligned with the minor axis direction of the elliptical polarized light. Through this, there are cases where the sensitivity of detection (a ratio of a change in a detection signal relative to a change in the exposure conditions) is improved.

The image capturing device 35 outputs an image signal of the wafer surface image to the image processing unit 40, the image processing unit 40 generates a digital image of the wafer surface, and information of that image is outputted to the inspection unit 60. Using this image information, the inspection unit 60 evaluates the exposure conditions and the like in the exposure device used when forming the repeating pattern 12 of the wafer 10. Note that the illumination-side polarizing filter 26 can also be rotated in order to shift the polarization direction of the illumination light ILI incident on the wafer surface from P-polarized light. However, even in this case, the polarization direction of the light receiving-side polarizing filter 32 is set to a crossed nicols state relative to the illumination-side polarizing filter 26. A combination of the wavelength $\lambda$ of the illumination light ILI and the angle of the illumination-side polarizing filter 26 when the digital image is generated in this manner is called a polarization condition. Note that it is also possible to provide a mechanism that, for example, changes the angle of incidence $\theta 3$ of the illumination light ILI (that is, the angle of reflection $\theta 3$), and in the case where the angle of incidence is changed in this manner, the angle of incidence is also included in a polarization condition. The aforementioned recipe information contains a plurality of polarization conditions.

Next, an example of a method in which light from a pattern in a wafer surface is detected and exposure conditions of the exposure device 100 used when the pattern is formed are evaluated using the evaluation device 1 according to the present embodiment will be described with reference to the flowchart in FIG. 5. Meanwhile, because it is necessary to find evaluation conditions in advance during this evaluation, an example of a method for finding those evaluation conditions (also called "condition setting" hereinafter) will be described with reference to the flowchart in FIG. 4. As an example, it is assumed here that diffraction inspection (inspection carried out by detecting the diffracted light beams ILD from the wafer 10) is carried out on the wafer surface using the evaluation device 1. Accordingly, as illustrated in FIG. 1A, the illumination-side polarizing filter 26 and the light receiving-side polarizing filter 32 are retracted from the optical path of the evaluation device 1. Furthermore, of the plurality of sets of exposure conditions including the dose quantity and the focal position of the exposure device 100, it is assumed that the dose quantity is evaluated.

Figure 4:
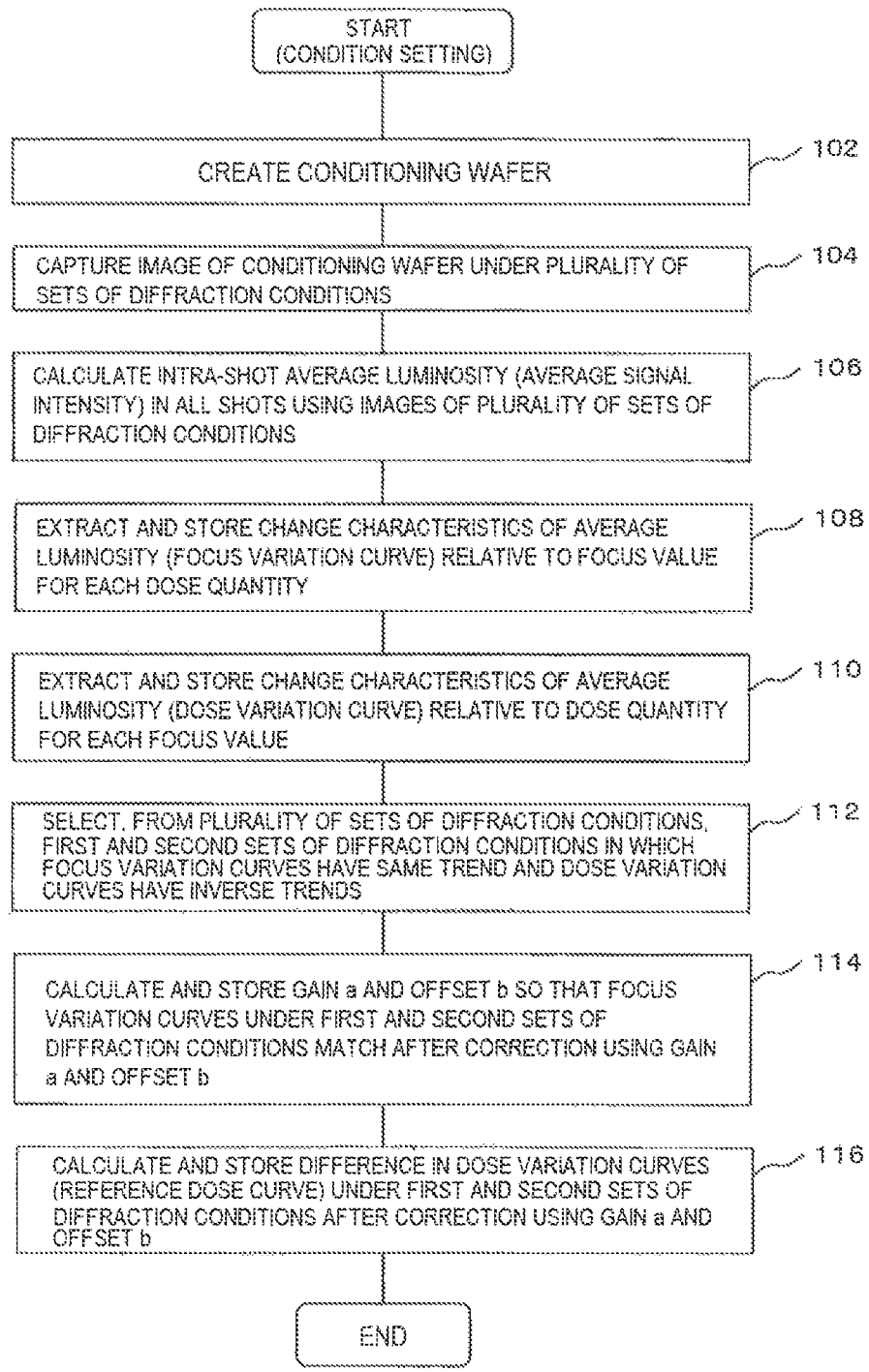
FIG. 4 is a flowchart illustrating an example of a method for finding evaluation conditions (condition setting).
Figure 6A:
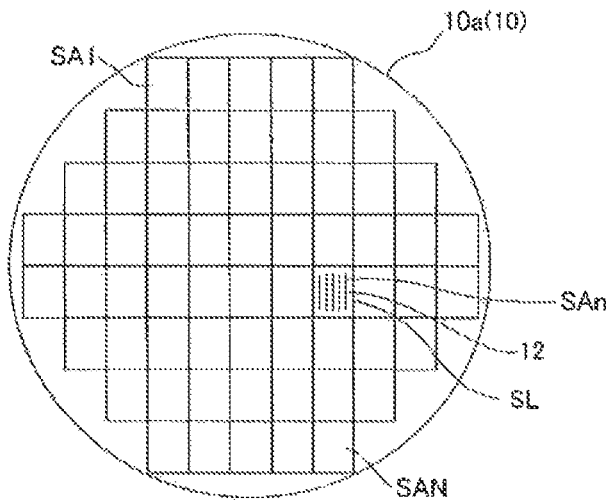
FIG. 6A is a plan view illustrating an example of a conditioning wafer 10.
Figures 6B, 6C:
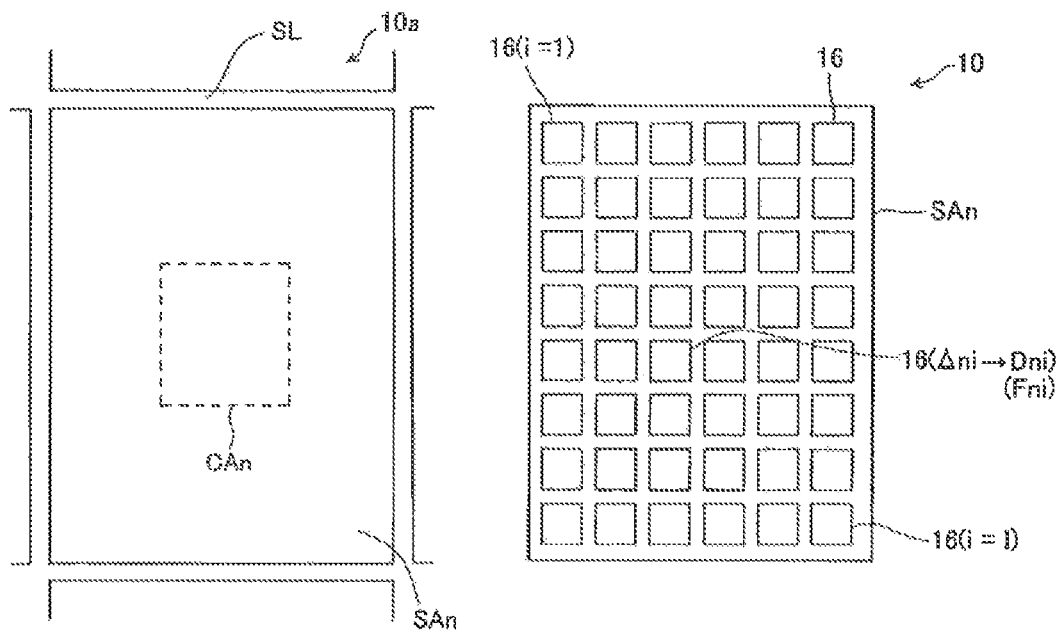
FIG. 6B is an enlarged view illustrating a single shot.
FIG. 6C is an enlarged view illustrating an example of a plurality of set regions in a shot.

First, for condition setting, in step 102 of FIG. 4 (creating a conditioning wafer), a wafer 10a in which, for example, N (where N is an integer from approximately 10 to 100, for example) shots SAn (where n=1 to N) are arranged with scribe line regions SL interposed therebetween, is prepared, as illustrated in FIG. 6A. The wafer 10a that has been coated with a resist is then transported to the exposure device 100 illustrated in FIG. 1B, after which the exposure device 100 exposes each shot SAn with a pattern of the same reticle (not illustrated) of an actual device while changing the exposure conditions such that, for example, the focal position is sequentially changed between shots arranged in a scanning direction used during scanning exposure of the wafer 10a (a longer direction of the shots) and the dose quantity is sequentially changed between shots arranged in a non-scanning direction orthogonal to the scanning direction (a shorter direction of the shots). At this time, a scanning speed during scanning exposure may be reduced, for example, in order to increase the precision with which the focal position and the dose quantity are controlled. Then, by developing the exposed wafer 10a, a wafer 10a in which the repeating pattern 12 has been formed under different exposure conditions in each of the shots SAn (called a conditioning wafer hereinafter) is produced.

Note that a plurality of patterns whose cycle directions are the same or orthogonal to each other are normally formed at a plurality of pitches in a reticle of an actual device, and even in each shot SAn, patterns having different pitches are also formed outside of the repeating pattern 12 having the pitch P. Furthermore, in the case where there is a pattern block in which, for example, the repeating patterns having the pitch P are arranged at a greater pitch P1 (>P), the same diffracted light beams are emitted from the pattern block as diffracted light beams emitted from the pattern having the pitch P1, and thus the diffraction inspection can be carried out substantially as if there is a pattern having the pitch P1.

Hereinafter, it is assumed that a defocus amount (called a focus value here) relative to a best focal position is used as the focal position (the best focal position refers to a position at which line width fluctuations are at a minimum when the focus is shifted ±; however, in the present specification, this refers to a best focal position set in the exposure device 100). With respect to the focal position, the focus value is set in five steps at 30 nm intervals, namely −60 nm, −30 nm, 0 nm, +30 nm, and +60 nm, for example. Focus value numbers 1 to 5 on a horizontal axis in FIG. 8A, which will be mentioned later, correspond to the five steps of the focus value (−60 to +60 nm). Note that it is also possible to set the focus value to a plurality of steps at 50 nm intervals, for example, and it is also possible to set the focus value to 17 steps at 25 nm intervals, for example, namely −200 to +200 nm, or the like.

Meanwhile, the dose quantity is set, for example, to nine steps at 1.5 mJ intervals (10.0 mJ, 11.5 mJ, 13.0 mJ, 14.5 mJ, 16.0 mJ, 17.5 mJ, 19.0 mJ, 20.5 mJ, and 22.0 mJ). Dose quantity numbers 1 to 9 on a horizontal axis in FIG. 8B, which will be mentioned later, correspond to the nine steps of the dose quantity (10.0 to 22.0 mJ). Note that an optimal exposure quantity required in the exposure of a pattern for an actual semiconductor device (a best dose) is approximately 5 to 40 mJ depending on the pattern, and thus it is desirable to vary the dose quantity at intervals of approximately 0.5 to 2.0 mJ central to the best dose for that pattern.

The conditioning wafer 10a according to the present embodiment is what is known as a FEM wafer (Focus Exposure Matrix wafer) in which dose quantities (exposure quantities or exposure energies) and focal positions are assigned in a matrix and the wafer is exposed and developed as the matrix. Note that a plurality of conditioning wafers 10a may be produced in the case where a number of shots in which different sets of exposure conditions are obtained by multiplying the number of steps of focus values and the number of steps of dose quantities is greater than the total number of shots in the surface of the conditioning wafer 10a.

Conversely, in the case where, for example, the number of shots SAn arranged in the scanning direction is greater than the number of steps across which the focus value is changed, and/or the case where the number of shots SAn arranged in the non-scanning direction is greater than the number of steps across which the dose quantity is changed, it is sufficient to expose only some of the shots among the shots arranged in the scanning direction and/or the non-scanning direction. However, in this case, a plurality of shots exposed while changing the focus value and the dose quantity may be provided as a plurality of sets in the scanning direction or the non-scanning direction, and measurement values obtained for shots having the same focus value and dose quantity may be averaged. Meanwhile, a plurality of shots having different focus values and dose quantities may be arranged at random so as to reduce the effects of unevenness in the application of the resist between a central portion and a peripheral portion of the wafer, the effects of differences in the scanning direction (the +Y direction or the −Y direction in FIG. 2B) of the wafer during scanning exposure, and the like, for example.

Once the conditioning wafer 10a is produced, the conditioning wafer 10a is transported onto the stage 5 of the evaluation device 1 illustrated in FIG. 1A. The control unit 80 then reads out a plurality of sets of diffraction conditions from the recipe information in the storage unit 85. It is assumed that the plurality of sets of diffraction conditions are, for example, the wavelength λ of the illumination light ILI being one of the aforementioned λ1, λ2, and λ3, and the tilt angle φ2 of the stage 5 being one of five angles D1 to D5 that meets the aforementioned formula (Formula 1), for 15 (=3×5) sets of conditions. Here, the set of diffraction conditions in which the wavelength λ is λn (n=1 to 3) and the tilt angle φ2 is Dm (m=1 to 5) is expressed as (n–Dm) in FIGS. 8A and 8B.

Figure 7:
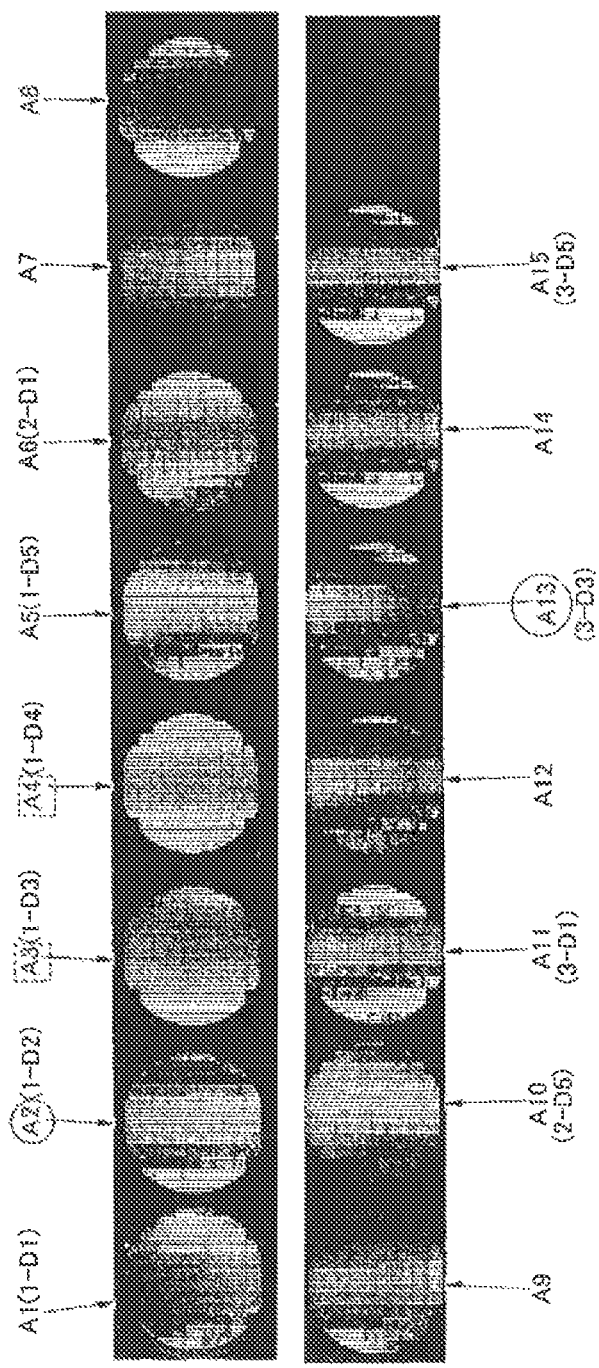
FIG. 7 is a diagram illustrating images of wafers captured under a plurality of sets of diffraction conditions.

Next, the sets of diffraction conditions are set to the 15 sets of conditions in sequence, with n=1 and m=1 to 5, n=2 and m=1 to 5, and n=3 and m=1 to 5, the surface of the conditioning wafer 10a is irradiated with the illumination light ILI under those respective sets of diffraction conditions, and the image capturing device 35 captures an image of the diffracted light beams from the conditioning wafer 10a and outputs an image signal to the image processing unit 40 (step 104). Note that the sets of diffraction conditions may be found through diffraction condition searching at this time. FIG. 7 illustrates an example of a luminosity distribution in images A1 to A15 of the conditioning wafer 10a, captured under those 15 sets of diffraction conditions (n–Dm).

Next, on the basis of the image signal of the conditioning wafer 10a inputted from the image capturing device 35, the image processing unit 40 generates a digital image of the entire surface of the conditioning wafer 10a for each of the plurality (15, here) of sets of diffraction conditions. Then, using the digital images corresponding to the plurality of sets of diffraction conditions, an average signal intensity is calculated by averaging the signal intensities of all of the pixels within all of the shots SAn in the conditioning wafer 10a excluding the scribe line regions SL (see FIG. 6B), and the result of the calculation is outputted to the inspection unit 60 (step 106). Note that the average signal intensity is also called a shot average luminosity (or an intra-shot average luminosity). The shot average luminosity is calculated in this manner in order to suppress the effects of aberration and the like in the projection optical system of the exposure device 100. Note that an average signal intensity (average luminosity) obtained by averaging the signal intensities in all of the pixels within, for example, a partial region CAn in a central portion of the shot SAn illustrated in FIG. 6B may be calculated in order to further suppress the effects of the aberration and the like.

However, it is also possible to find the effects of aberration (a distribution of an error imparted on the digital image) in the projection optical system in advance and correct the effects of the aberration when the digital image is generated. In this case, instead of the shot average luminosity, the average signal intensity (average luminosity) may be calculated for each of I (where I is an integer of several tens, for example) set regions 16 that are rectangular or the like (see FIG. 6C), and the subsequent processing may then be carried out using the average luminosity of the set regions 16 in the same locations within the shots SAn, for example. The arrangement of the set regions 16 is six rows in the scanning direction and five columns in the non-scanning direction, for example, but any desired size and arrangement may be used.

Figure 8A:
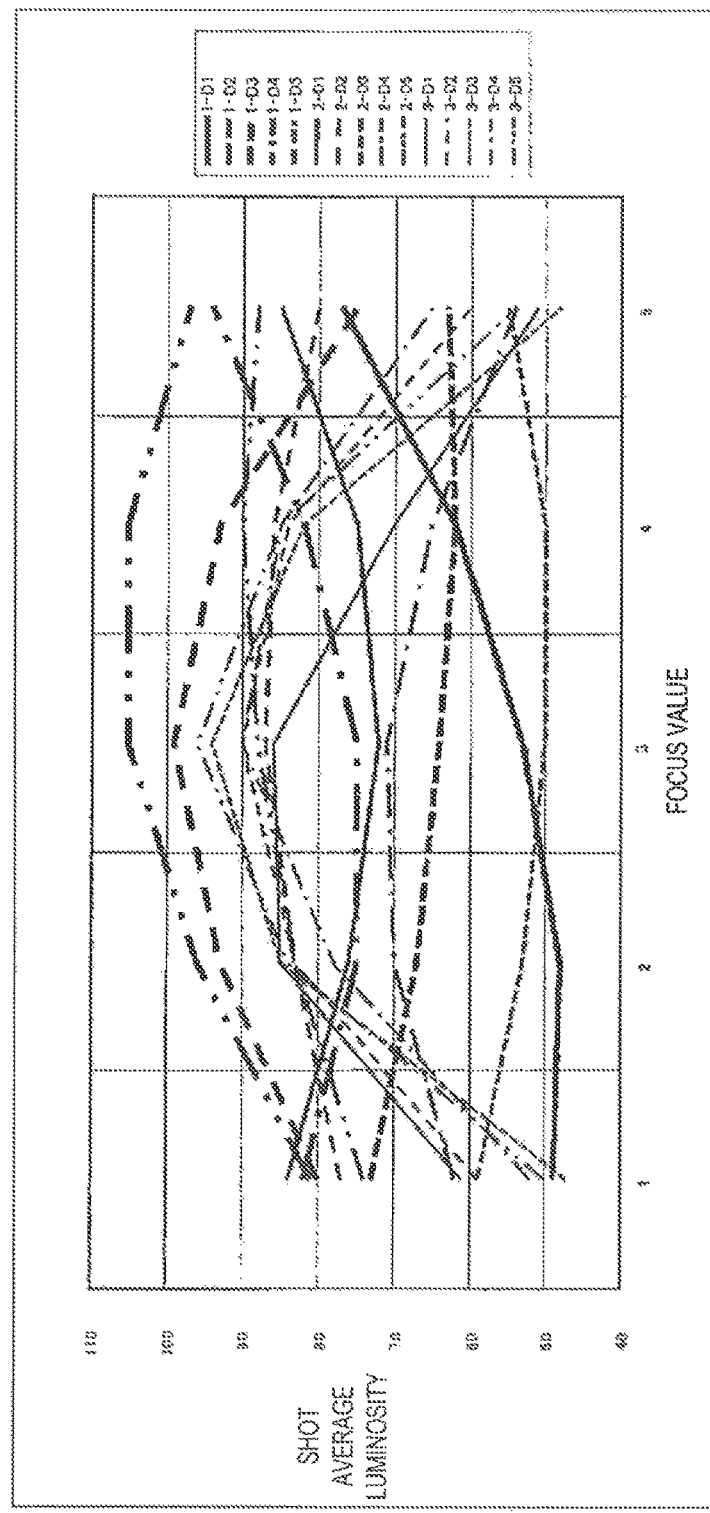
FIG. 8A is a diagram illustrating a plurality of focus variation curves.
Figure 8B:
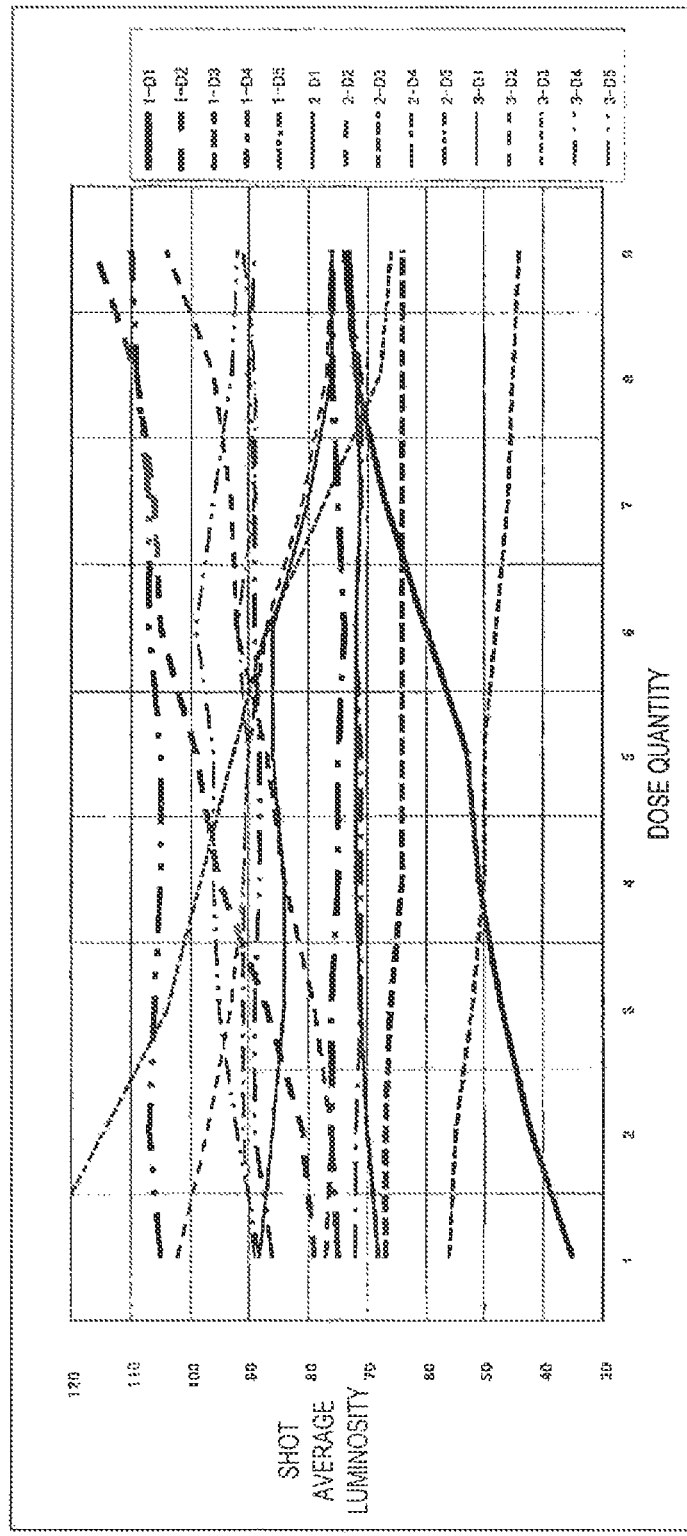
FIG. 8B is a diagram illustrating a plurality of dose variation curves.

Next, the first computation unit 60a in the inspection unit 60 extracts, from all of the shot average luminosities in the conditioning wafer 10a obtained for each of the plurality of sets of diffraction conditions (n–Dm), average luminosity change characteristics, expressed as a focus variation curve, found when the dose quantity is the same but the focus value is varied among the five steps as the exposure conditions, and stores the focus variation curve in the storage unit 85 (step 108). FIG. 8A illustrates a plurality (15, here) of focus variation curves obtained under the diffraction conditions (n–Dm) when the dose quantity here is at the best dose. The vertical axes in FIGS. 8A and 8B represent relative values of the shot average luminosities, whereas the horizontal axis in FIG. 8A represents the focus values from first to fifth steps (−100 to +100 nm).

In addition, the first computation unit 60a extracts, from all of the shot average luminosities obtained for each of the plurality of sets of diffraction conditions (n–Dm), average luminosity change characteristics, expressed as a dose variation curve, found when the focus value is the same but the dose quantity is varied among the nine steps as the exposure conditions, and stores the dose variation curve in the storage unit 85 (step 110). FIG. 8B illustrates a plurality of dose variation curves obtained under the diffraction conditions (n–Dm) when the focus value here is at 0 (the best focal position). The horizontal axis in FIG. 8B represents the dose quantity from the first to ninth steps (10.0 to 22.0 mJ).

Figure 9A:
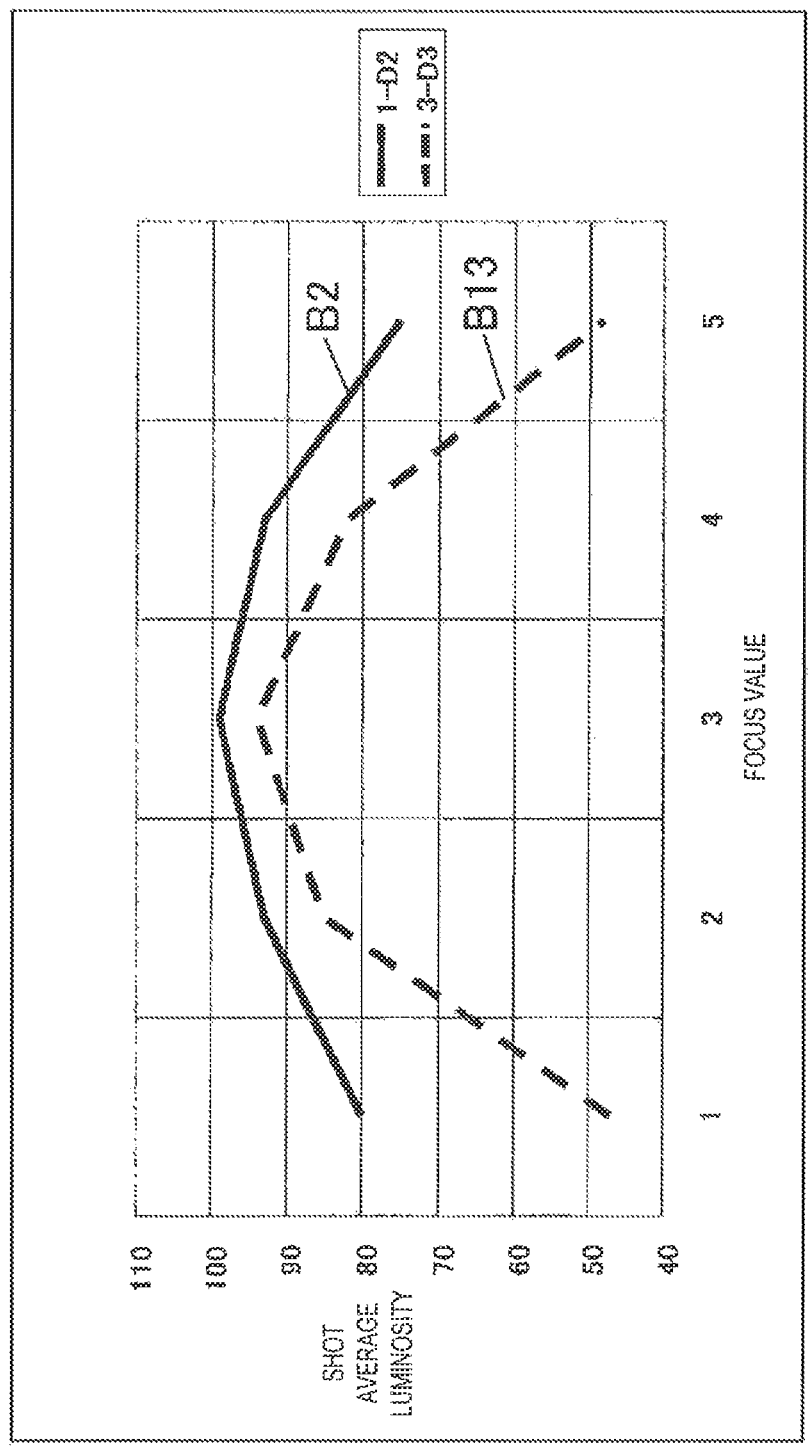
FIGS. 9A and 9B are diagrams each illustrating a focus variation curve and a dose variation curve measured under two diffraction conditions.
Figure 9B:
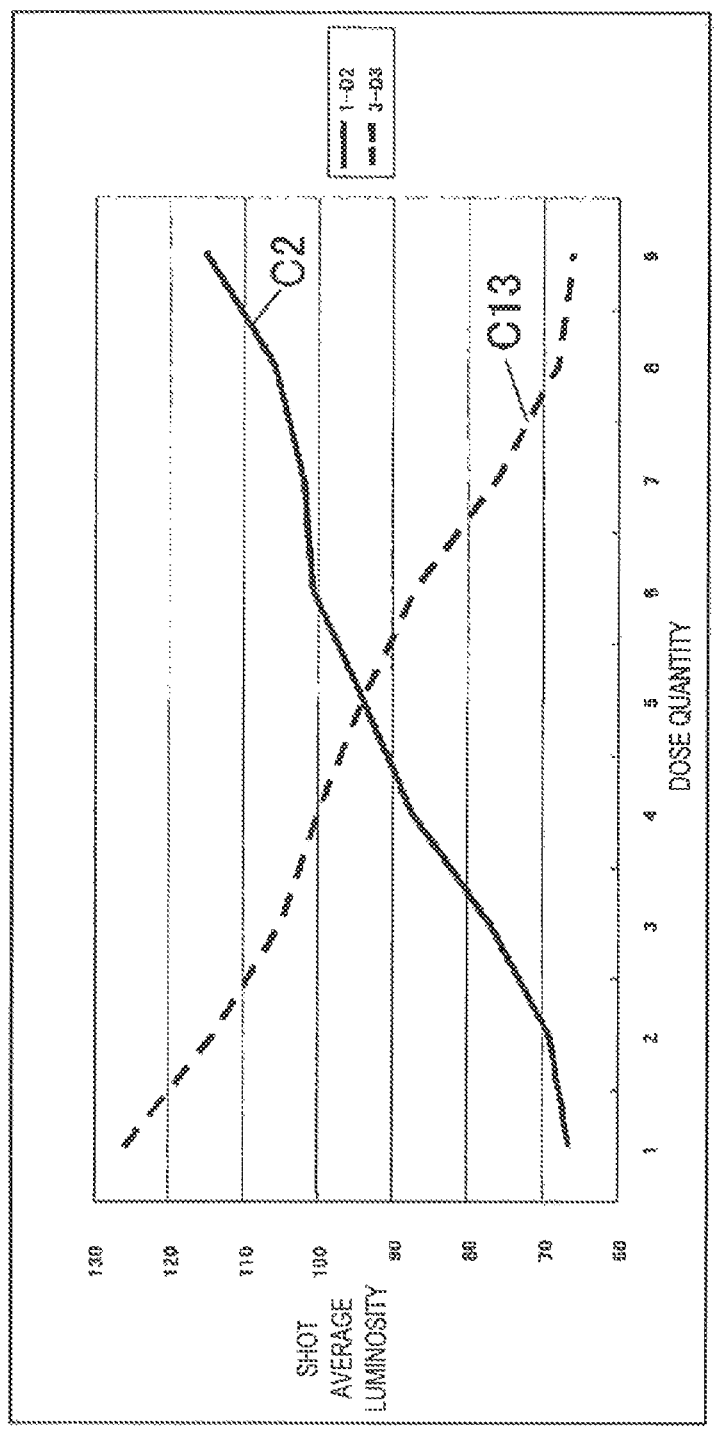

Then, the first computation unit 60a selects, from the aforementioned plurality of sets of diffraction conditions, first and second sets of diffraction conditions in which the focus variation curves have the same trend (characteristics in which both shot average luminosities increase or decrease in almost the same manner as the focus value increases, for example) and the dose variation curves have inverse trends (characteristics in which one shot average luminosity essentially increases and the other shot average luminosity essentially decreases as the dose quantity increases, for example), and stores the selected two sets of diffraction conditions in the storage unit 85 (step 112). In the present embodiment, (n=1, m=2) with (1–D2) and (n=3, m=3) with (3–D3) are selected as the first and second sets of diffraction conditions. FIG. 9A illustrates two focus variation curves B2 and B13, of the 15 focus variation curves illustrated in FIG. 8A, obtained under the diffraction conditions (1–D2) and (3–D3), whereas FIG. 9B illustrates two dose variation curves C2 and C13, of the 15 variation curves illustrated in FIG. 8B, obtained under the diffraction conditions (1–D2) and (3–D3). It can be seen that the focus variation curves B2 and B13 have the same trend of change, whereas the dose variation curves C2 and C13 have inverse trends of change.

Figure 10A:
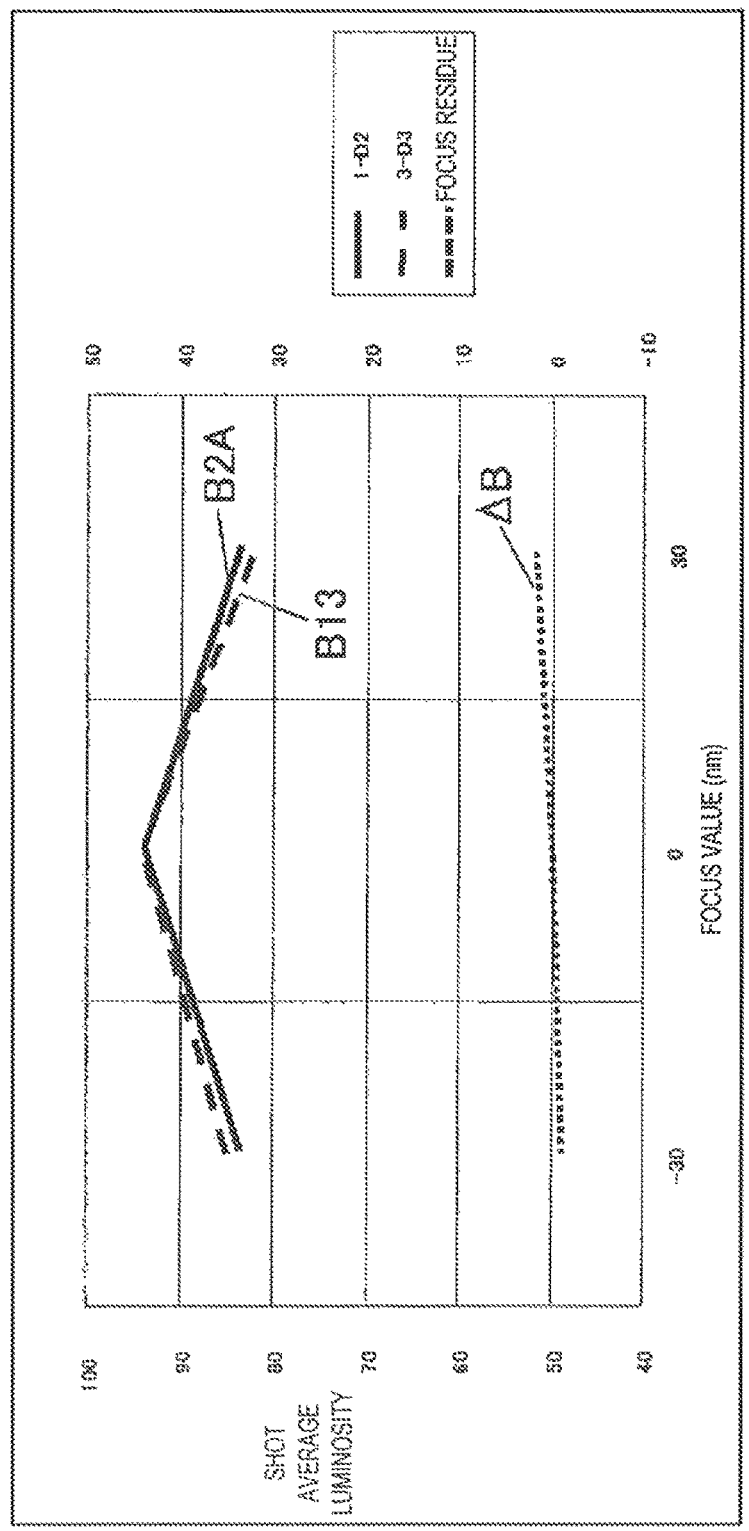
FIG. 10A is a diagram illustrating a focal position residue.

Next, the first computation unit 60a determines a gain a and an offset b at which a curve B2A (see FIG. 10A) obtained by using the gain a (any magnification or proportionality coefficient) and the offset b to correct the focus variation curve B2 obtained under the first diffraction conditions (1–D2) matches the focus variation curve B13 obtained under the second diffraction conditions (3–D3), or in other words, at which a difference (called focus residue hereinafter) ΔB between the corrected curve B2A and the focus variation curve B13 becomes a minimum, and stores the gain a and the offset b in the storage unit 85 (step 114). Note that the vertical axis on the right side in FIG. 10A represents a value of the focus residue ΔB. In this case, for example, the gain a and the offset b may be determined so that, when the focus values in the focus variation curves B2 and B13 are Fi (i=1 to 5) and represented by LB2 (Fi) and LB13 (Fi), an error that is a sum of squares of the next difference becomes a minimum. In the case of FIG. 9A, the value in the curve B2 is greater than the value in the curve B13, and thus the gain a has a value lower than 1. The integrating indicated in the following formula (Formula 2) is executed for the focus values Fi (i=1 to 5).

$$\text{ERROR} = \Sigma\{LB13(Fi) - (a \cdot LB2(Fi) + b)\}^2 \qquad \text{[Formula 2]}$$

Note that the values of the gain a and the offset b may be determined and stored for each reticle pattern that is subject to exposure.

In addition, a gain a' and an offset b' may be determined so that a curve obtained by using the gain a' (proportionality coefficient or magnification) and the offset b' to correct the focus variation curve B12 obtained under the second diffraction conditions (3–D3) and the focus variation curve B2 obtained under the first diffraction conditions (1–D2) match. Furthermore, the curve B2A and the focus variation curve B13 may be approximated using a higher-order polynomial (a fourth-order polynomial, for example) with respect to the focus value Fi, and the values of a and b may be determined so that a sum of squares of the difference between the two is at a minimum. In addition, the values of a and b may be determined so that one of the focus variation curves is corrected using only the gain a or the offset b, and the corrected curve matches the other focus variation curve to the greatest extent possible. Furthermore, a coefficient cfi that is multiplied with one of the focus variation curves so that the post-correction difference is 0 may be determined independently for each focus value Fi, for example.

Note that it is also possible to use two sets of diffraction conditions in which the characteristics of the two focus variation curves have an opposing trend (for example, one curve FA1 varies in a convex shape whereas the other curve FB1 varies in a concave shape relative to changes in a focus value Fx) and the characteristics of the dose variation curves have the same trend (for example, two curves DA1 and DB1 increase or decrease essentially monotonically relative to changes in the dose quantity). In this case, when the one curve FA1 is a function (fa(Fx)+fb1) (where fb is a constant), the other curve FB1 is essentially a function (−fb1·fa (Fx)+fb2) (where fb1 and fb2 are constants and fb1 is positive), and a gain a1 for matching the curve FB1 to the curve FA1 is a negative value of −1/fb1. Accordingly, the operation in the parentheses on the right side of the aforementioned formula (Formula 2) is, with respect to the gain a1, a sum of the curve FA1 and a value obtained by multiplying the curve FB1 by a constant (1/fb1).

Figure 10B:
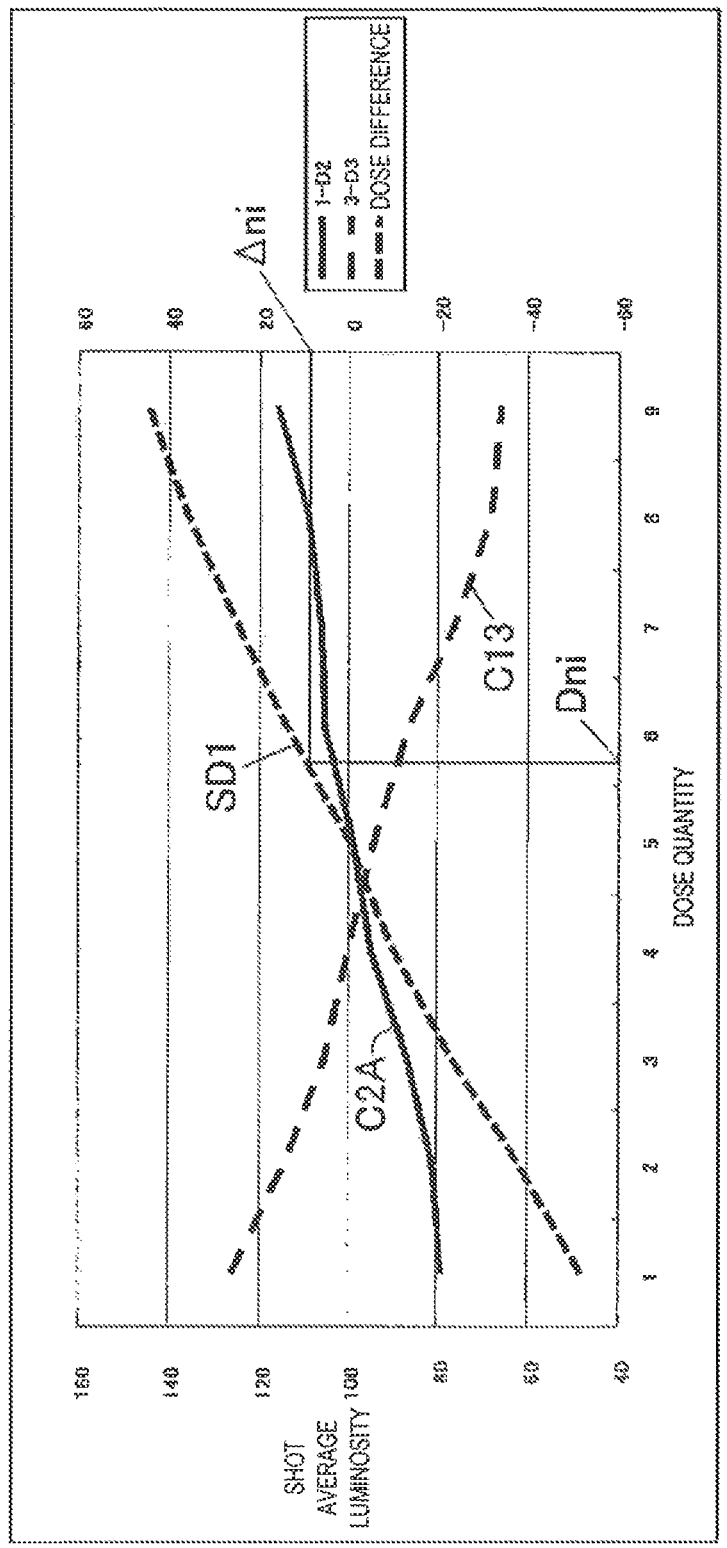
FIG. 10B is a diagram illustrating a dose quantity difference.
Figure 11A:
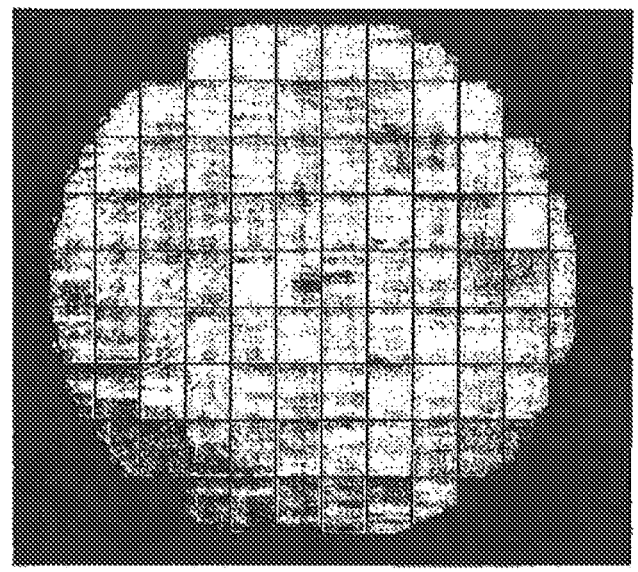
FIG. 11A is a diagram illustrating an example of a dose quantity distribution on a wafer surface.
Figure 11B:
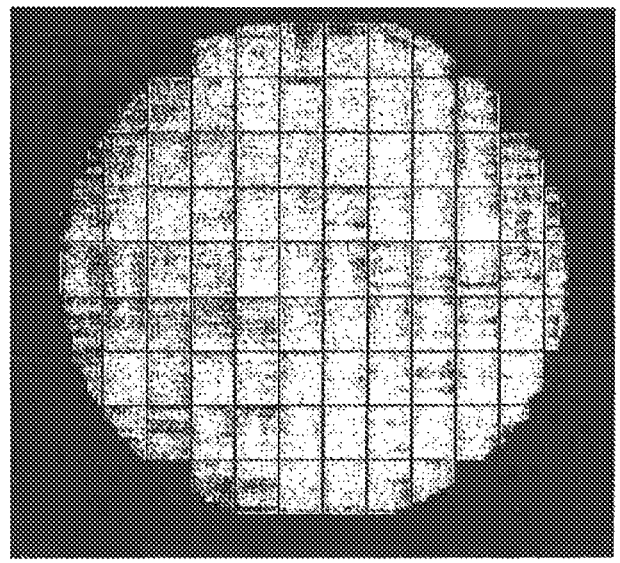
FIG. 11B is a diagram illustrating an example of focus values on the wafer surface.

Next, the first computation unit 60a calculates a curve (called a reference dose curve hereinafter) SD1 that expresses, as a function of the dose quantity, a difference (a dose difference) between a curve C2A (see FIG. 10B) obtained by using the gain a and the offset b calculated in step 114 to correct the dose variation curve C2 obtained under the first diffraction conditions (1–D2) indicated in FIG. 9B and the dose variation curve C13 obtained under the second diffraction conditions (3–D3); the calculated reference dose curve SD1 indicated in FIG. 10B is stored in the storage unit 85 (step 116). Note that the vertical axis on the right side in FIG. 10B represents a value of the dose difference. Meanwhile, the reference dose curve SD1 may also be approximated by a first-order expression or a higher-order polynomial regarding the dose quantity. The condition setting for finding the first and second sets of diffraction conditions, which are evaluation conditions used when evaluating the exposure conditions of the exposure device 100, is completed through the operations described thus far.

Next, the dose quantity in the exposure conditions of the exposure device 100 is evaluated as will be described hereinafter by carrying out diffraction inspection, using the two sets of diffraction conditions (1–D2) and (3–D3) found by the evaluation device 1 through the aforementioned condition setting, on a wafer in which a pattern has been formed through exposure by the exposure device 100 in an actual device manufacturing process. This evaluation operation can also be called dose monitoring. First, in step 120 of FIG. 5, a wafer 10 for actual exposure, having the same shot arrangement as that illustrated in FIG. 6A and that has been coated with a resist, is transported to the exposure device 100 illustrated in FIG. 1B; each shot SAn (where n=1 to N) of the wafer 10 is exposed by the exposure device 100 with a pattern placed in a reticle (not illustrated) of an actual device, and the exposed wafer 10 is then developed. The exposure conditions used at this time are, for all of the shots, a dose quantity corresponding to a best dose determined in accordance with that reticle, and a focal position corresponding to the best focal position.

However, in actuality, it is possible that variations in the dose quantity or the like will arise in each of the shots SAn in the wafer 10, and furthermore in each of the plurality of set regions 16 within each shot SAn, due to the effects of, for example, slight illumination unevenness in the non-scanning direction within a slit-shaped illumination region during scanning exposure in the exposure device 100, and therefore those dose quantities are evaluated. Furthermore, it is possible that variations in the focal position or the like will arise in each of the shots SAn, and furthermore in each of the plurality of set regions 16 within each shot SAn, due to the effects of vibrations or the like in the exposure device 100. In this case, if the diffraction inspection is simply carried out, the inspection result will also include parts caused by the focal position aside from the dose quantity, and thus the influence of the focal position is eliminated as follows.

The exposed and developed wafer 10 is loaded onto the stage 5 of the evaluation device 1 illustrated in FIG. 1A via the alignment mechanism, which is not illustrated (step 122). The control unit 80 then reads out the first and second sets of the diffraction conditions (1–D2) and (3–D3), determined through the aforementioned condition setting, from the recipe information in the storage unit 85. The diffraction conditions are set to the first and second sets of diffraction conditions in sequence, the surface of the wafer 10 is irradiated with the illumination light ILI under the respective sets of diffraction conditions, and the image capturing device 35 captures an image of the diffracted light beams from the wafer 10 and outputs the image signal to the image processing unit 40 (step 124).

Note that in step 104 of the condition setting process illustrated in the aforementioned FIG. 4, of the images A1 to A13 of the conditioning wafers obtained under the plurality of sets of diffraction conditions and illustrated in FIG. 7, the image obtained under the first set of diffraction conditions (1–D2) is the image A2 and the image obtained under the second set of diffraction conditions (3–D3) is the image A13. Accordingly, the luminosities of the images of the respective parts of the wafer 10 captured under the first and second sets of diffraction conditions are, in the images A2 and A13, essentially the same as the luminosities of the images in parts in the conditioning wafer where the dose quantity and the focus value in the corresponding parts of the wafer 10 are essentially the same.

Next, the image processing unit 40 generates the digital image of the entire surface of the wafer 10 for each of the first and second sets of diffraction conditions, on the basis of the image signals of the wafer 10 inputted from the image capturing device 35. Then, using the respective corresponding digital images obtained under the first and second sets of diffraction conditions, the average signal intensity (average luminosity) is calculated for every 1 set regions 16 (see FIG. 6C) in all of the shots SAn in the wafer 10, and the result of the calculation is outputted to the inspection unit 60 (step 126). Note that regions corresponding to the respective pixels in the image capturing element of the image capturing device 35 may be used instead of the set regions 16. Here, the average luminosities obtained in an ith set region 16 within an nth shot under the first and second sets of diffraction conditions are taken as $L1ni$ and $L2ni$, respectively (where n=1 to N and i=1 to I). Each of these average luminosities includes two values, of the focus variation curve and the dose variation curve.

Then, for each of all the set regions 16 in the wafer 10, the third computation unit 60c in the inspection unit 60 calculates an average luminosity difference $\Delta ni$ by subtracting the average luminosity $L2ni$ obtained under the second set of diffraction conditions (3–D3) from a luminosity $L1ni'$ obtained by using the gain a and the offset b calculated in the aforementioned step 114 to correct the average luminosity $L1ni$ obtained under the first set of diffraction conditions (1–D2), and stores the result of the calculation in the storage unit 85 (step 128). Components corresponding to the post-correction focus variation curves B2A and B13 indicated in FIG. 10A are almost completely eliminated from the difference $\Delta ni$, whereas only a component corresponding to a difference between the post-correction dose variation curves C2A and C13 indicated in FIG. 10B almost completely remains.

Accordingly, for each of all the set regions 16 in the wafer 10, the third computation unit 60c applies the aforementioned average luminosity difference $\Delta ni$ to the reference dose curve SD1 stored in the aforementioned step 116 and indicated in FIG. 10B and calculates or estimates a corresponding dose quantity $Dni$, and stores the result of the calculation or the result of the estimation in the storage unit 85 (step 130). A component caused by the focal position is eliminated from the dose quantity $Dni$ calculated or estimated in this manner. Thereafter, the control unit 80 converts the dose quantity $Dni$ to a brightness, for example (or a color may be changed) and displays a dose distribution (a distribution expressed by the image in FIG. 11A, for example) for the entire surface of the wafer 10 in a display device (not illustrated) (step 132). Furthermore, information of the dose distribution for the entire surface of the wafer 10 is provided from the signal output unit 90 to the exposure device 100 via the host computer 600 under the control of the control unit 80 (step 134). In response, a control unit (not illustrated) of the exposure device 100 finds a distribution of a difference between that dose distribution and the best dose, for example, and in the case where the distribution of the difference exceeds a predetermined range of tolerance, corrects a distribution of a width of an illumination region in the scanning direction during scanning exposure, for example. This reduces an error in the dose distribution during subsequent exposures.

According to this embodiment, by carrying out diffraction inspection under two sets of diffraction conditions using a wafer 10 on which a pattern for an actual device has been formed, a dose quantity in the exposure conditions for the exposure device 100 used when forming the pattern can be estimated or evaluated with high precision while eliminating the effects of the focal position.

As described above, the evaluation device 1 according to the present embodiment includes: the illumination system 20 that illuminates the wafer 10, which has a non-planar repeating pattern 12 (structure) provided through exposure under a plurality of sets of exposure conditions including a dose quantity and a focal position (the first and second sets of exposure conditions), with illumination light; the light-receiving system 30 and the imaging unit 35 (a detection unit) that detect light coming from a surface (the exposed surface) of the wafer 10 due to the illumination light; and the computation unit 50 that calculates or estimates the dose quantity when exposing the wafer 10 on the basis of a computation result obtained by carrying out a computation for suppressing an amount of change relative to a change in the focus on a detection result obtained by the imaging unit 35 under the first and second sets of diffraction conditions (the evaluation conditions) in which at least one of the illumination conditions (the wavelength λ or the like) of the illumination system 20 and the detection conditions (the tilt angle φ2 of the stage 5 or the like) of the light-receiving system 30 and the imaging unit 35 differs.

Meanwhile, an evaluation method that uses the evaluation device 1 includes: step 124 of illuminating the wafer 10 with the illumination light and detecting light coming from the surface of the wafer 10 in which the repeating pattern 12 has been formed due to the illumination light; and steps 128 and 130 of calculating or estimating a dose quantity during exposure of the wafer 10 on the basis of a computation result obtained by carrying out an operation for suppressing an amount of change relative to a change in the focal position on a detection result obtained by detecting the light coming from the surface under the first and second sets of diffraction conditions in which at least one of the illumination conditions of the illumination light and the detection conditions of the light coming from the surface of the wafer 10 is different.

According to this embodiment, using the wafer 10 that has the non-planar repeating pattern 12 provided through exposure under a plurality of sets of exposure conditions serving as a plurality of sets of processing conditions, the dose quantity in the plurality of sets of exposure conditions can be estimated or evaluated with high precision in a state where the effects of the focal position are suppressed. Meanwhile, it is not necessary to use a separate measurement pattern, and the exposure conditions can be evaluated by detecting light from a wafer in which a pattern of an actual device has been formed, which makes it possible to efficiently and with high precision evaluate the exposure conditions with respect to a pattern that is actually exposed.

In addition, the evaluation method includes: step 102 of creating the conditioning wafer 10a (an evaluation substrate) by exposing a wafer for evaluation while changing at least one of the dose quantity and the focal position and providing the repeating pattern 12 in a plurality of shots on the surface of the wafer; steps 104 and 106 of illuminating the surface of the wafer 10a on which the repeating pattern 12 has been provided with illumination light and detecting light coming from the surface due to the illumination light; steps 108 to 112 of using a plurality of detection results obtained by detecting the light coming from the surface of the conditioning wafer 10a under the first and second sets of diffraction conditions among which at least one of the illumination conditions of the illumination light and the detection conditions of the light coming from the surface of the wafer 10a is different in order to find in advance and store the first and second sets of diffraction conditions that produce a detection result in which the amount of change relative to a change in the focal position can be suppressed; and step 114 of finding and storing coefficients (the gain a and the offset b) of an arithmetic expression applied to two detection results obtained under the first and second sets of diffraction conditions.

Accordingly, by finding the first and second sets of diffraction conditions in advance, the exposure conditions for a wafer in which is formed a pattern of an actual device can be evaluated efficiently, performing only two measurements thereafter.

Meanwhile, the device manufacturing system DMS (exposure system) according to the present embodiment includes the exposure device 100 (an exposure unit) having the projection optical system that exposes the surface of the wafer with a pattern and the evaluation device 1 according to the present embodiment, and corrects the exposure conditions (processing conditions) in the exposure device 100 on the basis of the first set of exposure conditions (first set of processing conditions) estimated by the computation unit 50 of the evaluation device 1.

Meanwhile, an exposure method (processing method) according to the present embodiment includes providing a pattern on a surface of a wafer through exposure (step 120), estimating the first set of exposure conditions for the wafer using the evaluation method according to the present embodiment (steps 122 to 130), and correcting the exposure conditions when exposing the wafer in accordance with the first set of exposure conditions estimated through the evaluation method (step 134).

By correcting the exposure conditions in the exposure device 100 in accordance with the first set of exposure conditions estimated by the evaluation device 1 or through the evaluation method used thereby in this manner, the exposure conditions in the exposure device 100 can be efficiently and with high precision set to a desired state using a wafer used for actually manufacturing a device.

Figure 12A:
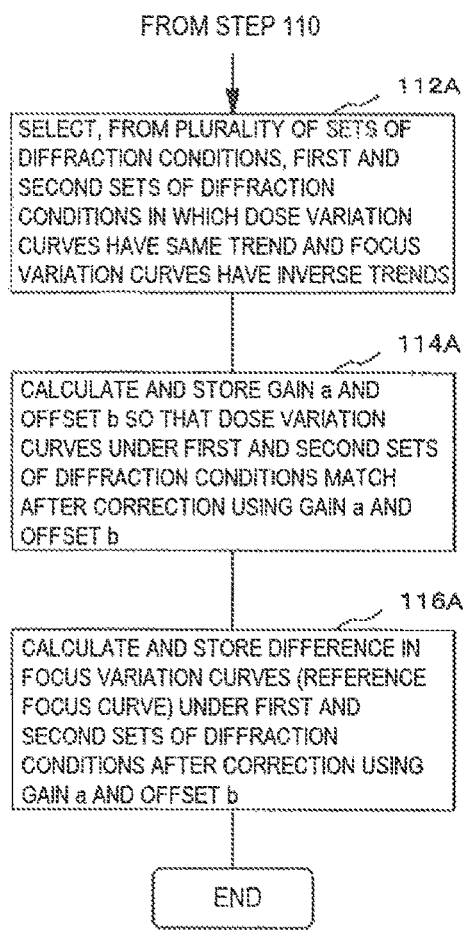
FIG. 12A is a flowchart illustrating primary parts in another example of condition setting.
Figure 12B:
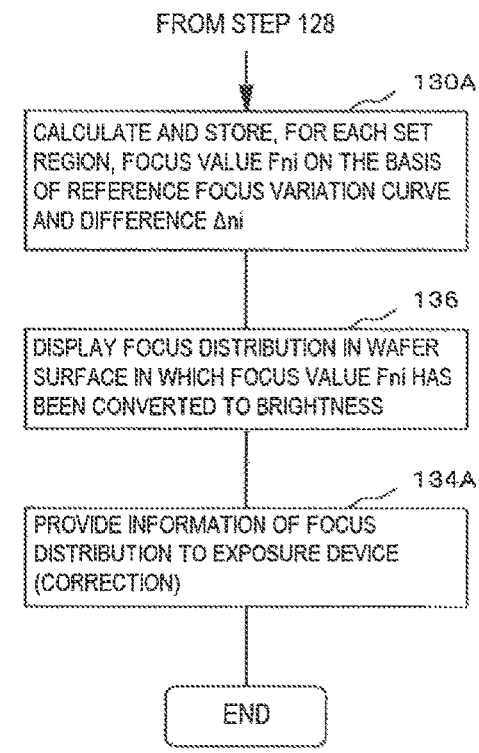
FIG. 12B is a flowchart illustrating primary elements of a focus value evaluation method.

Although the aforementioned embodiment describes evaluating the dose quantity while suppressing the effects of the focal position, note that it is also possible to evaluate the focal position while suppressing the effects of the dose quantity, as illustrated in the flowchart of FIGS. 12A and 12B, which illustrates the primary parts of a variation. This evaluation operation can also be called focus monitoring. According to this variation, in step 112A of FIG. 12A, which follows step 110 of FIG. 4, the second computation unit 60b of the inspection unit 60 illustrated in FIG. 1A selects, from the plurality of sets of diffraction conditions, first and second sets of diffraction conditions in which the dose variation curves have the same trend and the focus variation curves have inverse trends, and stores the selected two sets of diffraction conditions in the storage unit 85. Here, (n=1, m=3) with (1−D3) and (n=1, m=4) with (1−D4) are selected as the first and second sets of diffraction conditions.

Note that in step 104 of the condition setting process illustrated in the aforementioned FIG. 4, of the images A1 to A13 of the conditioning wafers obtained under the plurality of sets of diffraction conditions and illustrated in FIG. 7, the image obtained under the first diffraction conditions (1−D3) is the image A3 and the image obtained under the second diffraction conditions (1−D4) is the image A4. Accordingly, the luminosities of the images of the respective parts of the wafer 10 captured under the first and second sets of diffraction conditions are, in the images A3 and A4, essentially the same as the luminosities of the images in parts in the conditioning wafer where the dose quantity and the focus value in the corresponding parts of the wafer 10 are essentially the same.

Figure 13A:
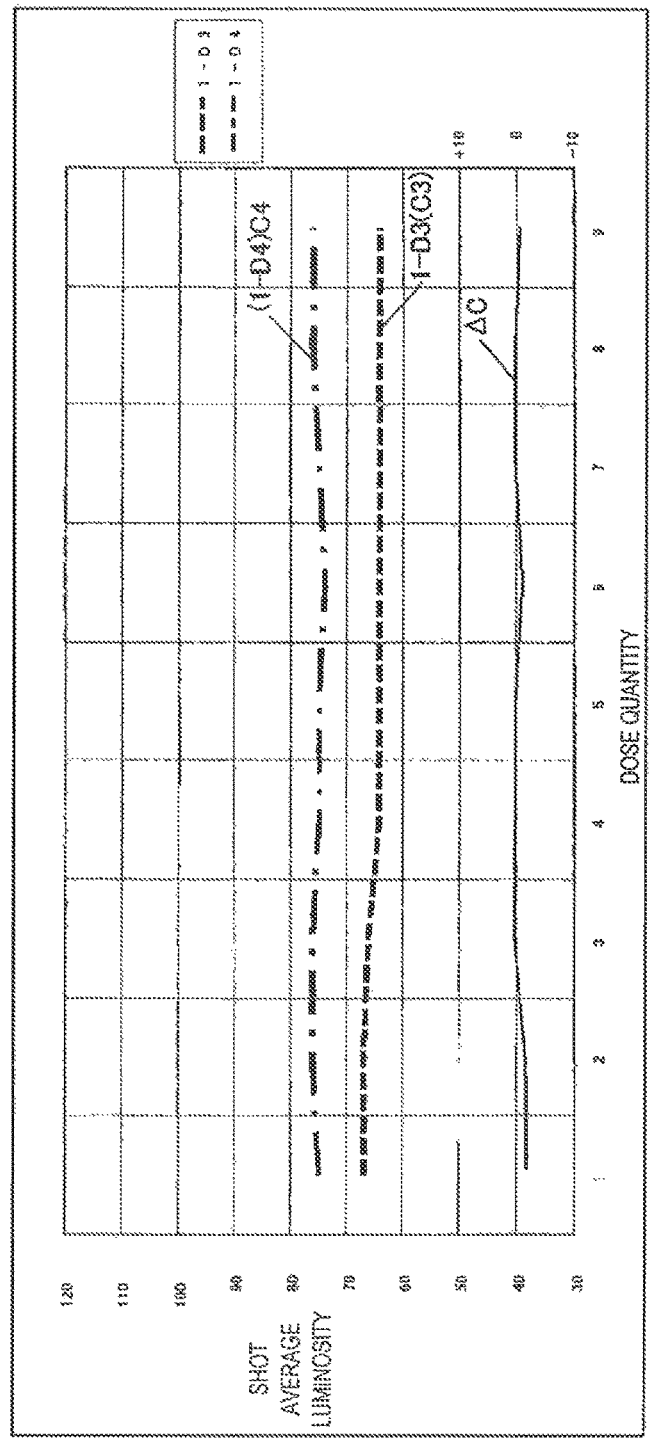
FIGS. 13A and 13B are diagrams each illustrating a dose variation curve and a focus variation curve measured under two sets of diffraction conditions.
Figure 13B:
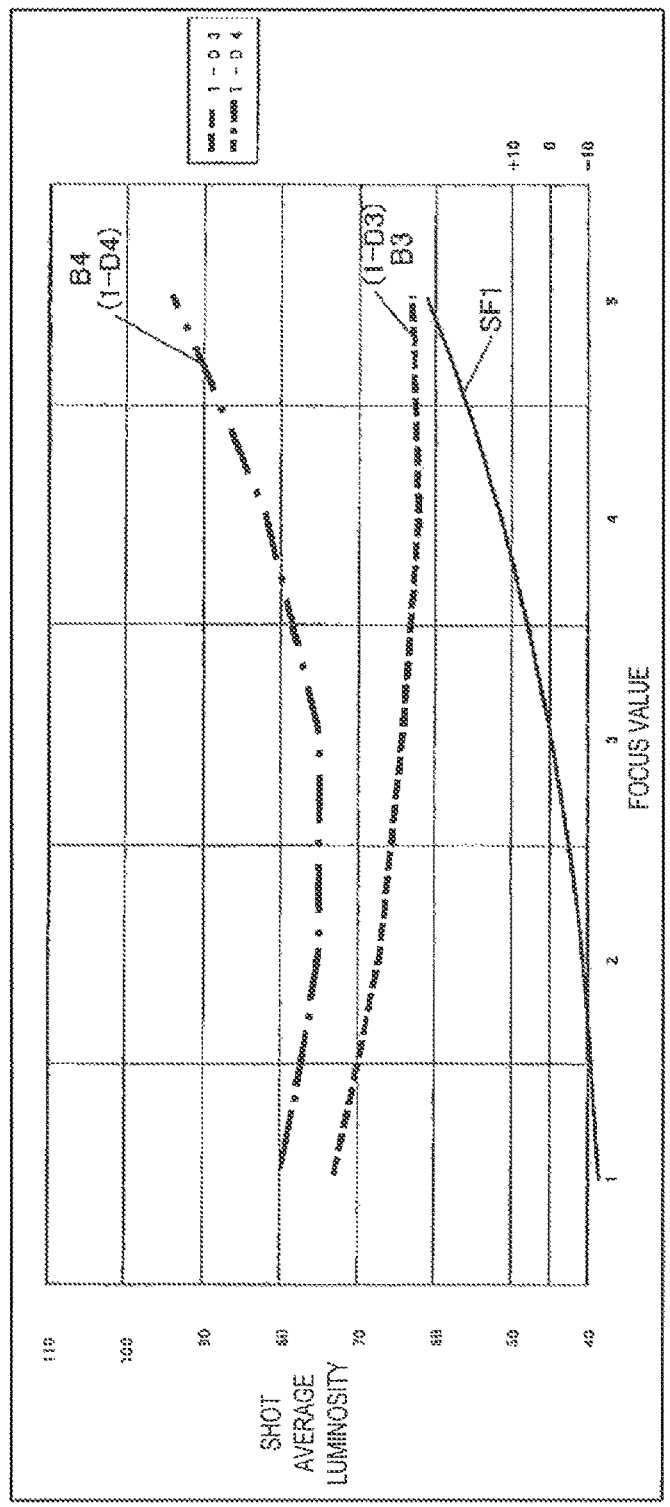

FIG. 13A illustrates two dose variation curves C2 and C4, of the 15 dose variation curves illustrated in FIG. 8B, obtained under the diffraction conditions (1−D3) and (1−D4), whereas FIG. 13B illustrates two focus variation curves B3 and B4, of the 15 variation curves illustrated in FIG. 8A, obtained under the diffraction conditions (1−D3) and (1−D4). It can be seen that the dose variation curves C2 and C4 have the same trend of change, whereas the focus variation curves B3 and B4 have inverse trends of change. Note that in a range where the focus value is low, an absolute value of a negative slope of the focus variation curve B3 is greater than an absolute value of a negative slope of the focus variation curve B4; as such, in the overall range of the focus value, the slope of the curve B3 is less than the slope of the curve B4, and the curves B3 and B4 can be considered to be changing in inverse trends.

Next, the second computation unit 60b determines the gain a and the offset b so that a curve (not illustrated) obtained by using the gain a and the offset b to correct the dose variation curve C3 obtained under the first diffraction conditions (1–D3) and the dose variation curve C4 obtained under the second diffraction conditions (1–D4) match, or in other words, so that a sum of squares of a residue ΔC between the corrected curve and the dose variation curve C4 is at a minimum, and stores the gain a and the offset b in the storage unit 85 (step 114A). Note that the vertical axis on the right side in FIG. 13A represents a value of the residue ΔC.

Next, the second computation unit 60b calculates a curve (called a reference focus curve hereinafter) SF1 that expresses, as a function of the focus value, a difference (a focus difference) between a curve (not illustrated) obtained by using the gain a and the offset b calculated in step 114A to correct the focus variation curve B3 obtained under the first diffraction conditions (1–D3) indicated in FIG. 13B and the focus variation curve B4 obtained under the second diffraction conditions (1–D4); the calculated reference focus curve SF1 is stored in the storage unit 85 (step 116). Note that the vertical axis on the right side in FIG. 10B represents a value of the focus difference. Meanwhile, the reference focus curve SF1 may also be approximated by a first-order expression or a higher-order polynomial regarding the focus value.

Figure 5:
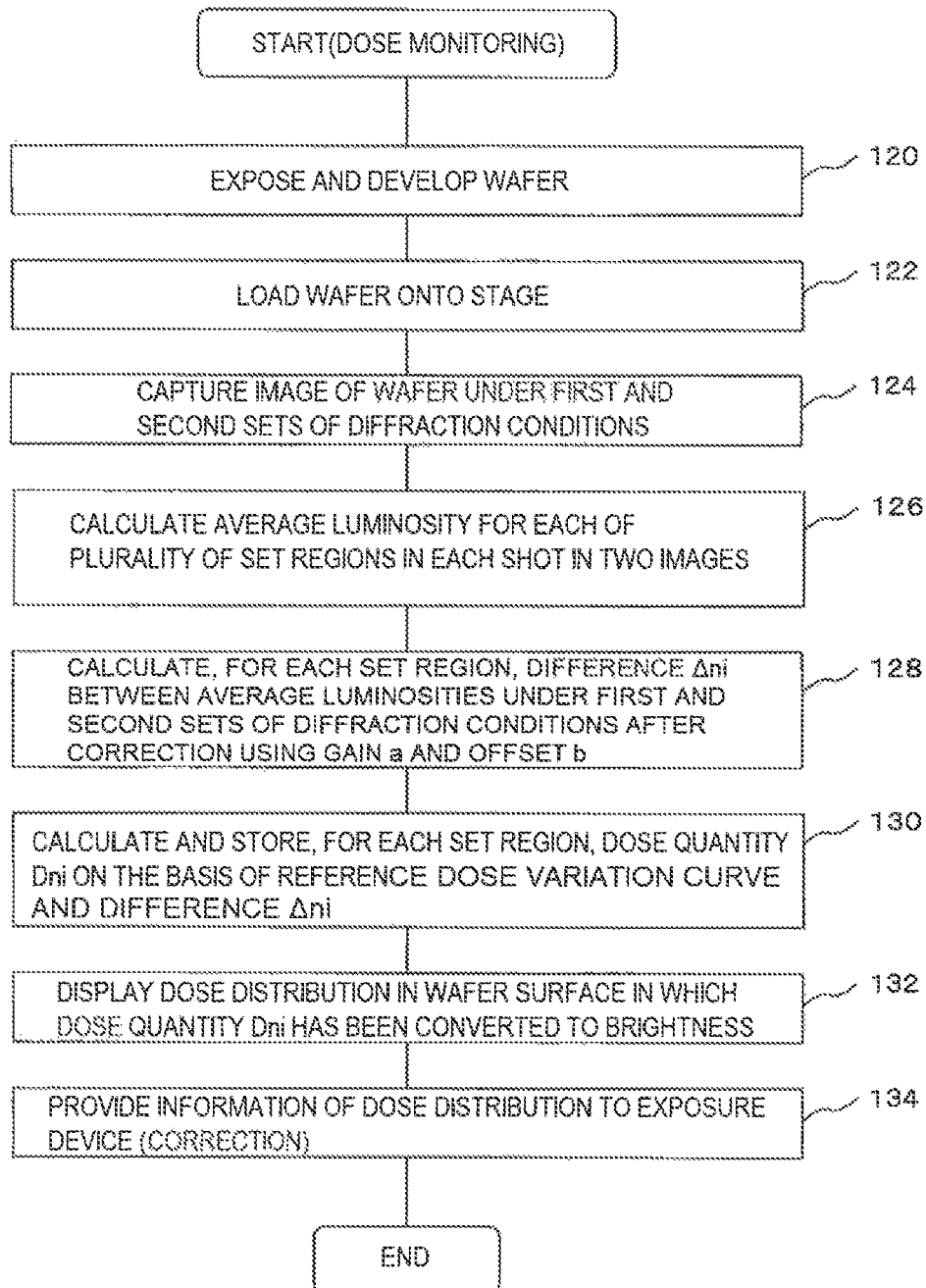
FIG. 5 is a flowchart illustrating a method for evaluating a dose quantity.

Then, in the case where the focal position, serving as one of the exposure conditions of the wafer, is to be evaluated through diffraction inspection of the wafer exposed and developed by the exposure device 100, in step 124 of FIG. 5, an image of the wafer 10 is captured under the first and second diffraction conditions (1–D3) and (1–D4) selected in step 112A, and in step 128 of FIG. 5, two average luminosity difference Δni obtained under the first and second sets of diffraction conditions are calculated using the gain a and the offset b stored in step 114A, for each set region in the wafer 10. After step 128, in step 130A illustrated in FIG. 12B, for each of all the set regions 16 in the wafer 10, the third computation unit 60c of the inspection unit 60 applies the aforementioned average luminosity difference Δni to the reference focus curve SF1 stored in the aforementioned step 116A and indicated in FIG. 13B and calculates or estimates a corresponding focus value Fni. The calculation result or the estimation result is stored in the storage unit 85. A component caused by the dose quantity is eliminated from the focus value Fni calculated or estimated in this manner.

Thereafter, the control unit 80 converts the focus value Fni to a brightness, for example (or a color may be changed) and displays a focus distribution (a distribution expressed by the image in FIG. 11B, for example) for the entire surface of the wafer 10 in the display device (not illustrated) (step 136). Furthermore, information of the focus distribution for the entire surface of the wafer 10 is provided from the signal output unit 90 to the exposure device 100 under the control of the control unit 80 (step 134A). In response, the control unit (not illustrated) of the exposure device 100 finds a distribution of a difference between that focus distribution and the best focal position, for example, and in the case where the distribution of the difference exceeds a predetermined range of tolerance, adjusts (corrects) an auto focus mechanism (not illustrated) or the like, for example. This reduces an error in the focus distribution during subsequent exposures.

In the aforementioned embodiment, a computation is carried out for suppressing the effects of one of the exposure conditions on the average luminosities obtained from images of the wafer obtained under two sets of diffraction conditions. Instead, a computation may be carried out for suppressing the effects of one of the exposure conditions on, for example, three or more luminosities obtained from images of the wafer obtained under three or more sets of diffraction conditions, and the other of the exposure conditions may then be found from this computation result.

Furthermore, although the aforementioned embodiment describes inspecting the exposure conditions using diffraction inspection on the wafer surface carried out by the evaluation device 1, the exposure conditions may be inspected using PER inspection (inspection based on changes in the polarization state of reflected light beams) on the wafer surface carried out by the evaluation device 1.

Meanwhile, in the aforementioned embodiment, the first and second sets of diffraction conditions (or polarization conditions) in which, for example, the focus variation curves have the same trends and the dose variation curves have inverse trends are selected from the plurality of sets of diffraction conditions (or polarization conditions), and thus the selection of the first and second sets of diffraction conditions (or polarization conditions) is easy. Instead, the first and second sets of diffraction conditions (or polarization conditions) may be selected from the plurality of sets of diffraction conditions (or polarization conditions) so that, for example, a difference (or a sum of squares of the difference) between the detection results under these conditions and a change in the dose quantity is greater than a difference (or a sum of squares of the difference) between the detection results under these conditions and a change in the focus value.

Furthermore, although the aforementioned embodiment describes evaluating the dose quantity and the focal position as the exposure conditions, the diffraction inspection or the PER inspection according to the aforementioned embodiment may be used in order to evaluate a wavelength of exposure light in the exposure device 100, illumination conditions (a coherence factor (σ value), for example), a numerical aperture of a projection optical system PL, a temperature of a liquid when carrying out immersion exposure, or the like as the exposure conditions.

[Second Embodiment]

A second embodiment will be described in reference to FIGS. 14A to 15B. In the present embodiment as well, the device manufacturing system DMS illustrated in FIG. 1B is used, and the evaluation device 1 illustrated in FIG. 1A is used to evaluate the processing conditions. Meanwhile, in the present embodiment, the processing conditions are evaluated for a wafer in which a fine-pitched repeating pattern has been formed using what is known as spacer double patterning (or sidewall double patterning).

Figure 14A:
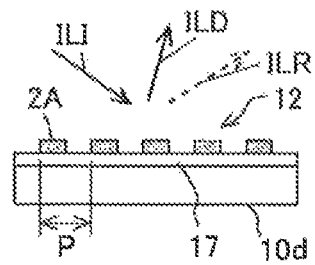
FIG. 14A is an enlarged cross-sectional view illustrating primary parts of a wafer.
Figure 14B:
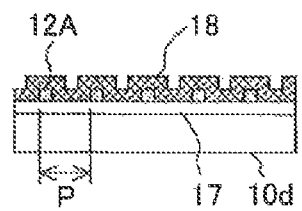
FIG. 14B is an enlarged cross-sectional view illustrating primary parts of another wafer.
Figure 14C:
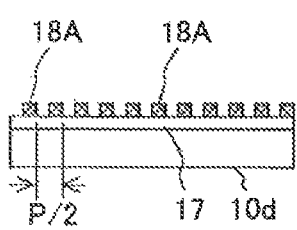
FIG. 14C is an enlarged cross-sectional view illustrating a wafer following a process illustrated in FIG. 14B.
Figure 14D:
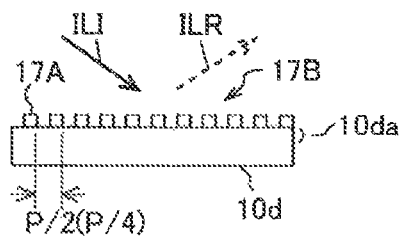
FIG. 14D is an enlarged cross-sectional view illustrating part of a pattern formed in the wafer.

In spacer double patterning, first, a repeating pattern 12 in which line portions 2A of a plurality of resist patterns are arranged at a pitch P is formed by, for example, coating the surface of a hard mask layer 17 of a wafer 10d with a resist and then exposing and developing a pattern using the exposure device 100, as illustrated in FIG. 14A. In the present embodiment, it is assumed that the pitch P is close to a resolution limit of the exposure device 100. Then, as illustrated in FIG. 14B, the line portions 2A are slimmed to create line portions 12A having ½ the line width, and a spacer layer 18 is deposited by a thin-film forming device (not illustrated) so as to cover the line portions 12A. Then, as illustrated in FIG. 14C, after etching only the spacer layer 18 of the wafer 10*d* using an etching device 300, a repeating pattern in which a plurality of spacer portions 18A having a line width of almost P/4 are arranged at a pitch P/2 is formed on the hard mask layer 17 by using the etching device 300 to remove only the line portions 12A. Then, as illustrated in FIG. 14D, a repeating pattern 17B in which hard mask portions 17A having a line width of almost P/4 are arranged at the pitch P/2 is formed by etching the hard mask layer 17 using the plurality of spacer portions 18A as a mask. After this, for example, a repeating pattern having a pitch corresponding to almost ½ the resolution limit of the exposure device 100 can be formed by etching a device layer 10*da* of the wafer 10*d* using the repeating pattern 17B as a mask. Furthermore, a repeating pattern having a pitch of P/4 can also be formed by repeating the aforementioned processes.

Meanwhile, in the case where diffraction inspection is carried out using the evaluation device 1, it is necessary for the pitch of the repeating pattern to be no less than ½ the wavelength λ of the illumination light ILI of the evaluation device 1 in order to produce diffraction. Accordingly, in the case where light at a wavelength of 248 nm is used as the illumination light, the diffracted light beams ILD are not produced by a repeating pattern 12 whose pitch P is less than 124 nm. Accordingly, the diffraction inspection becomes progressively more difficult as the pitch P approaches the resolution limit of the exposure device 100, as in the case illustrated in FIG. 14A. Furthermore, only the directly-reflected light beams ILR are produced with the repeating pattern 17B having a pitch of P/2 (and furthermore, of P/4), as in the case illustrated in FIG. 14D, which makes diffraction inspection difficult. However, in the case where a pattern block in which the repeating patterns 17B are arranged at a greater pitch is present, diffracted light beams can be detected from this pattern block, and thus diffraction inspection is possible.

In the present embodiment, PER inspection (inspection based on changes in the polarization state of reflected light beams) is carried out on the wafer surface by the evaluation device 1 in order to detect light from the wafer 10*d* in which the repeating pattern 17B that does not produce diffracted light beams is formed in each shot, as illustrated in FIG. 14D, and evaluate the processing conditions of the repeating pattern 17B. Hereinafter, condition setting that selects a plurality of polarization conditions used when carrying out PER inspection will be described with reference to the flowchart illustrated in FIG. 15A, and a method for evaluating processing conditions in the device manufacturing system DMS by carrying out PER inspection using the selected polarization conditions will be described with reference to the flowchart illustrated in FIG. 15B. Note that in FIGS. 15A and 15B, steps that correspond to those in FIGS. 4 and 5 will be given the same or similar reference numerals, and descriptions thereof will be omitted or simplified.

Here, in order to carry out PER inspection of the surface of the wafer 10*d* in which the repeating pattern 17B having the pitch P/2 has been formed using the evaluation device 1, the illumination-side polarizing filter 26 and the light receiving-side polarizing filter 32 are inserted into the optical path of the evaluation device 1 and the tilt angle of the stage 5 on which the wafer 10*d* is placed is set so that the light-receiving system 30 can receive the directly-reflected light beams ILR from the wafer 10*d* irradiated with the illumination light ILI from the illumination system 20, as illustrated in FIG. 2A. Meanwhile, the angle of rotation of the stage 5 is set so that the cycle direction of the repeating pattern 17B intersects with an incidence direction of the illumination light ILI at 45 degrees, for example. Then, 15 sets of conditions (λa, θb) (where a=1 to 3 and b=0 to 4), which are sets of a wavelength λa of the illumination light ILI (one of the aforementioned λ1 to λ3) and an angle θb of the illumination-side polarizing filter 26 (for example, an angle of rotation of a polarization axis relative to the cycle direction of the repeating pattern, with the angle of rotation of 35 degrees+5 degrees×b (where b=0 to 4), are assumed as a plurality of sets of polarization conditions, as one example. However, when switching the angle of the illumination-side polarizing filter 26, the angle of the light receiving-side polarizing filter 32 is also switched so as to maintain the crossed nicols state with respect to the illumination-side polarizing filter 26. Furthermore, the present embodiment assumes, as processing conditions in the device manufacturing system DMS for the repeating pattern 17B, a depositing time ts (a thin-film depositing amount) for the spacer layer 18 illustrated in FIG. 14B and an etching time te (an etching amount) for the spacer layer 18, with the etching time te evaluated while suppressing the effects of the depositing time ts.

First, to carry out condition setting, in step 102A of FIG. 15, the spacer double patterning process illustrated in FIGS. 14A to 14D is executed 25 (=5×5) times for the combinations of five types of depositing times ts (ts3 to ts7) and five types of etching times te (te3 to te7) so as to form the repeating pattern 17B in each shot of 25 conditioning wafers (not illustrated). Note that it is assumed that the depositing time ts5 is a best depositing time (correct amount), and the etching time te5 is a best etching time (correct etching amount). In this case, the etching times te3 and te4 represent insufficient etching, whereas the etching times te6 and te7 represent excessive etching.

The plurality of (25, here) conditioning wafers that have been produced are then transported onto the stage 5 of the evaluation device 1 illustrated in FIG. 2A. Then, for each of the plurality of conditioning wafers, the surface of the conditioning wafer is irradiated with the illumination light ILI under the aforementioned plurality of (15, here) sets of polarization conditions (λa, θb), and the image capturing device 35 captures an image produced by the directly-reflected light beams ILR from the conditioning wafers and outputs an image signal to the image processing unit 40 (step 104A). Because 15 images are captured for each of the 25 conditioning wafers here, a total of 375 (=25×15) digital images are obtained by the image processing unit 40.

Furthermore, for the plurality of sets of polarization conditions, the image processing unit 40 uses the respective corresponding digital images and calculates an average signal intensity (average luminosity) by averaging the signal intensities of all of the pixels within all of the shots in the conditioning wafer (or regions in the central portions of the shots), and outputs the calculation result to the inspection unit 60 (step 106A).

Then, the first computation unit 60*a* in the inspection unit 60 extracts, as a spacer variation curve (not illustrated), change characteristics of the average luminosity when, of the processing conditions, the depositing amount (depositing time ts) is changed among five steps while keeping the etching amount (etching time te) the same, from the average luminosities of all of the conditioning wafers obtained under the plurality of sets of polarization conditions (λa and θb), and stores the spacer variation curve in the storage unit 85 (step 108A). In addition, the first computation unit 60*a* extracts, as an etching variation curve (not illustrated), change characteristics of the average luminosity when, of the processing conditions, the etching amount is changed among five steps while keeping the depositing amount the same, from all of the average luminosities obtained under the plurality of sets of polarization conditions (λa and θb), and stores the etching variation curve in the storage unit 85 (step 110A).

Figure 14E:
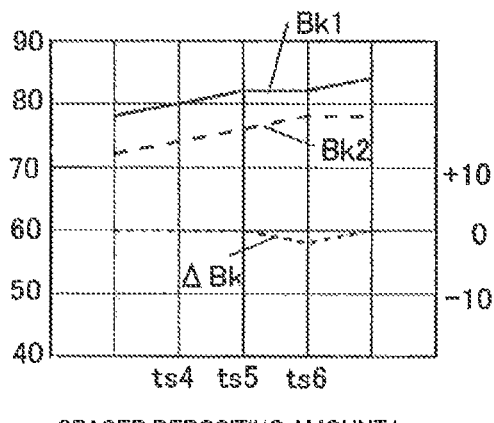
FIG. 14E is a diagram illustrating two spacer variation curves and residues thereof.
Figure 14F:
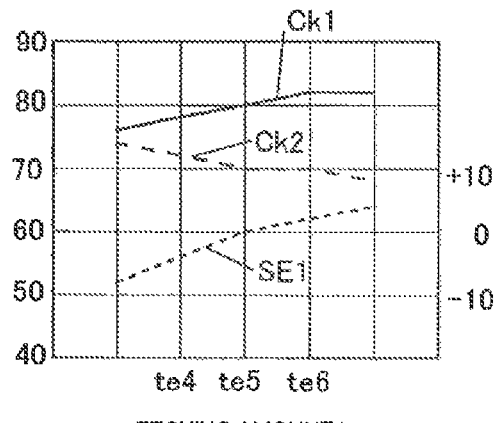
FIG. 14F is a diagram illustrating two etching variation curves and a difference therebetween.

Then, the first computation unit 60a selects, from the aforementioned plurality of sets of polarization conditions (λa, ηb), first and second sets of polarization conditions in which the spacer variation curves have the same trend (characteristics in which both average luminosities increase or decrease in essentially the same manner as the depositing time ts increases, for example) and the etching variation curves have inverse trends (characteristics in which one average luminosity essentially increases and the other average luminosity essentially decreases as the etching time te increases, for example), and stores the selected two sets of polarization conditions in the storage unit 85 (step 112B). FIG. 14E illustrates two variation curves Bk1 and Bk2, of the 15 spacer variation curves, obtained under the first and second sets of polarization conditions, and FIG. 14F illustrates two variation curves Ck1 and Ck2, of the 15 etching variation curves, obtained under the first and second sets of polarization conditions. The variation curves Bk1 and Bk2 have the same trend of change, whereas the variation curves Ck1 and Ck2 have inverse trends of change.

Next, the first computation unit 60a determines a gain a and an offset b at which a variation curve (not illustrated) obtained by using the gain a and the offset b to correct the spacer variation curve Bk1 obtained under the first polarization conditions matches the spacer variation curve Bk2 obtained under the second polarization conditions, or in other words, at which a difference ΔBk between the corrected curve and the curve Bk2 becomes a minimum through the least-squares method, and stores the gain a and the offset b in the storage unit 85 (step 114B). Note that the vertical axis on the right side in FIG. 14E represents a value of the difference ΔBk. Note that in the case where the value of the difference ΔBk becomes comparatively high in some areas, a different gain a' and offset b' may be applied to those areas only.

Next, the first computation unit 60a calculates a curve (called a reference etching curve hereinafter) SE1 that expresses, as a function of the etching time te (etching amount), a difference between a curve (not illustrated) obtained by using the gain a and the offset b calculated in step 114B to correct the etching variation curve Ck1 obtained under the first polarization conditions indicated in FIG. 14F and the etching variation curve Ck2 obtained under the second polarization conditions; the calculated reference etching curve SE1 is stored in the storage unit 85 (step 116B). Note that the vertical axis on the right side in FIG. 14F represents a value of the reference etching curve SE1. Meanwhile, the reference etching curve SE1 may also be approximated by a first-order expression or a higher-order polynomial regarding the etching time te. The condition setting for finding the first and second sets of polarization conditions, which are evaluation conditions used when evaluating the processing conditions, is completed through the operations described thus far.

Next, the etching amount in the processing conditions is evaluated in the following manner by the evaluation device 1 carrying out polarized light inspection on the wafer 10d in which the repeating pattern 17B has been formed using the device manufacturing system DMS in an actual device manufacturing process. This evaluation operation can also be called etching monitoring. First, in step 138 of FIG. 15B, the device manufacturing system DMS manufactures the wafer 10d in which the repeating pattern 17B is formed in each shot by executing the spacer double patterning process described with reference to FIGS. 14A to 14D. The processing conditions at this time are, in all of the shots, the best depositing time (correct amount) for the spacer depositing amount (depositing time ts) and the best etching amount (correct amount) for the etching amount (etching time te). However, in reality, there is a risk that variations will occur in the spacer depositing amount due to film thickness unevenness in the thin-film forming device (not illustrated), and a risk that variations will occur in the etching amount due to etching unevenness in the etching device 300. In this case, if the polarized light inspection is simply carried out, the inspection result will also include parts caused by the spacer depositing amount aside from the etching amount, and thus the influence of the spacer depositing amount is eliminated as follows.

The manufactured wafer 10d is loaded onto the stage 5 of the evaluation device 1 illustrated in FIG. 2A via the alignment mechanism, which is not illustrated (step 122A). Then, in the evaluation device 1, an image of the wafer 10d is captured under the first and second sets of polarization conditions determined through the aforementioned condition setting, and an image signal is outputted to the image processing unit 40 (step 124A).

Next, the image processing unit 40 generates digital images of the entire surface of the wafer 10d for each of the first and second sets of polarization conditions. Then, using the respective corresponding digital images obtained under the first and second sets of polarization conditions, the average signal intensity (average luminosity) is calculated for each of the plurality of set regions 16 (see FIG. 6C) in all of the shots in the wafer 10d, and the result of the calculation is outputted to the inspection unit 60 (step 126). Then, for each of all the set regions 16 in the wafer 10d, the third computation unit 60c in the inspection unit 60 calculates an average luminosity difference Δni by subtracting the average luminosity obtained under the second set of polarization conditions from a luminosity obtained by using the gain a and the offset b calculated in the aforementioned step 114B to correct the average luminosity obtained under the first set of polarization conditions, and stores the result of the calculation in the storage unit 85 (step 128). Components corresponding to the spacer variation curves Bk1 and Bk2 indicated in FIG. 14E are almost completely eliminated from the difference Δni, whereas a component corresponding to a difference between the post-correction etching variation curves Ck1 and Ck2 indicated in FIG. 14F almost completely remains.

Accordingly, for each of all the set regions 16 in the wafer 10d, the third computation unit 60c applies the aforementioned average luminosity difference Δni to the reference etching curve SE1 stored in the aforementioned step 116B and indicated in FIG. 14F and calculates or estimates a corresponding etching amount (etching time) teni, and stores the result of the calculation or the result of the estimation in the storage unit 85 (step 140). A component caused by the spacer depositing time eliminated from the etching amount teni calculated or estimated in this manner. Thereafter, the control unit 80 converts the etching amount teni to a brightness, for example (or a color may be changed) and displays etching unevenness for the entire surface of the wafer 10d in a display device (not illustrated) (step 142). Furthermore, information of the etching unevenness for the entire surface of the wafer 10 is provided from the signal output unit 90 to the etching device 300 via the host computer 600 under the control of the control unit 80 (step 144). In response, a control unit (not illustrated) of the etching device 300 finds a distribution of a difference between that etching unevenness and the correct etching amount, for example, and in the case where the distribution of the difference exceeds a predetermined range of tolerance, carries out correction by adjusting an etching unit or the like, for example. Through this, the etching unevenness can be reduced when executing the subsequent step 138 (the spacer double patterning process), and the repeating pattern 17B having the pitch P/2 can be manufactured with high precision.

According to this embodiment, by carrying out PER inspection under two sets of polarization conditions using a wafer 10d in which the repeating pattern 17B for an actual device has been formed, an etching amount for the etching device 300 used when forming the pattern can be estimated or evaluated with high precision while eliminating the effects of the spacer depositing amount.

In the same manner, by carrying out the PER inspection under the two sets of polarization conditions, the spacer depositing amount can be estimated or evaluated with high precision while eliminating the effects of the etching amount.

Meanwhile, in addition to the etching amount and the spacer depositing amount, a dose quantity, a focal position, and the like during exposure by the exposure device 100, for example, can also be considered as processing conditions in the double patterning process.

In addition, although the aforementioned embodiments describe the exposure device 100 as a scanning stepper that uses an immersion exposure method, the same effects as described above can be achieved by applying the aforementioned embodiments even in the case where an exposure device such as a dry-type scanning stepper or stepper is used as the exposure device 100. Furthermore, the aforementioned embodiments can also be applied in the case where an EUV exposure device that uses EUV light (extreme ultraviolet light) at a wavelength of less than 100 nm as the exposure light, an electron beam exposure device that uses an electron beam as an exposure beam, or the like is used as the exposure device 100.

Figure 16:
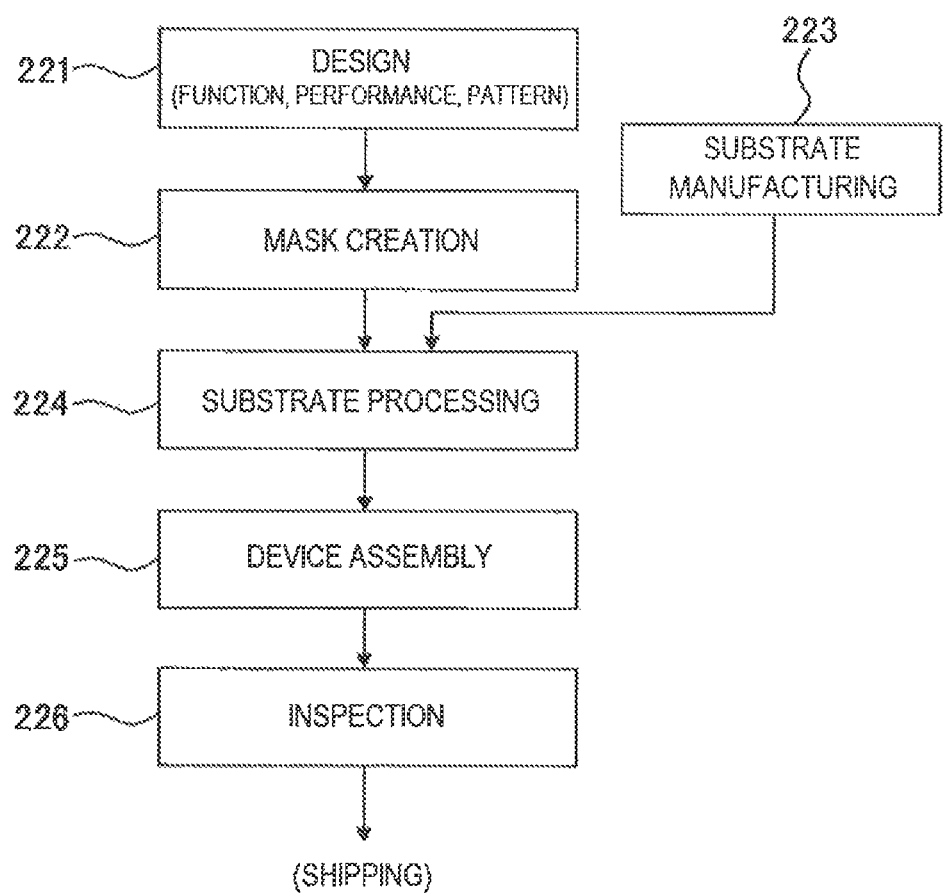
FIG. 16 is a flowchart illustrating a method for manufacturing a semiconductor device.

Meanwhile, as illustrated in FIG. 16, a semiconductor device (not illustrated) is manufactured through the following: a design process of designing functions and capabilities of the device (step 221); a mask manufacturing process of manufacturing a mask (a reticle) based on the design process (step 222); a substrate manufacturing process of manufacturing a substrate for a wafer from a silicon material or the like (step 223); a substrate processing process of forming a pattern in the wafer using the device manufacturing system DMS or a pattern forming method that uses that system (step 224); an assembly process, including a dicing process, a bonding process, a packaging process, and the like, for assembling the device (step 225); an inspection process of inspecting the device (step 226); and the like. A process of coating the wafer with a resist using the device manufacturing system DMS, a lithography process including an exposure process of exposing the wafer with a pattern in the reticle using the exposure device 100 in the device manufacturing system DMS and a developing process of developing the wafer, and an evaluating process of using the evaluation device 1 to evaluate the exposure conditions and the like using light from the wafer are executed in the substrate processing process (step 224).

In such method for manufacturing a semiconductor device, by using the aforementioned evaluation device 1 to evaluate exposure conditions and the like and then correcting the exposure conditions and the like on the basis of a result of the evaluation, for example, a favorable state is achieved for the manufacturing process, and the yield of semiconductors ultimately manufactured can be improved.

Although the device manufacturing method according to the present embodiment describes a method for manufacturing a semiconductor device in particular, the device manufacturing method according to the present embodiment can also be applied in, for example, the manufacture of devices that use materials aside from semiconductor materials, such as liquid crystal panels, magnetic disks, and the like, in addition to devices that use semiconductor materials.

Note that the present disclosure is not intended to be limited to the aforementioned embodiments, and a variety of configurations can be employed without departing from the essential spirit of the present disclosure.

REFERENCE SIGNS LIST

1 Evaluation device
5 Stage
10 Wafer
10a Conditioning wafer
20 Illumination system
30 Light-receiving system
35 Imaging unit
40 Image processing unit
50 Computation unit
60 Inspection unit
85 Storage part
100 Exposure device
DMS device manufacturing system

The invention claimed is:

1. An evaluation device comprising:
an illumination unit that illuminates, with illumination light, a substrate having a structure formed with a plurality of sets of processing conditions including first and second sets of processing conditions;
a detection unit that detects diffracted light beams coming from a processed surface of the substrate due to the illumination light;
a stage on which the substrate is mountable;
an estimating unit that estimates at least one of the first set of processing conditions and the second set of processing conditions at the time of processing the substrate, based on a detection result of the diffracted light beams obtained by the detection unit under a plurality of sets of evaluation conditions among which diffraction conditions differ; and
a controller configured to control a relative movement between the stage and one of the illumination unit and the detection unit, such that the detection unit detects the diffracted light beams under the plurality of sets of evaluation conditions among which diffraction conditions differ.

2. The evaluation device according to claim 1, wherein the plurality of sets of evaluation conditions include first and second sets of evaluation conditions; and
the estimating unit estimates at least one of the first set of processing conditions and the second set of processing conditions on the basis of a difference between the detection result obtained under the first set of evaluation conditions and the detection result obtained under the second set of evaluation conditions.

3. The evaluation device according to claim 2, wherein the difference is a difference after carrying out at least one of a process of adding an offset and a process of applying any magnification to at least one detection value in the detection result obtained under the first set of evaluation conditions and the detection result obtained under the second evaluation conditions.

4. The evaluation device according to claim 1, wherein
processing the substrate includes exposing the substrate through a projection optical system,
one of the first and second sets of processing conditions is an exposure quantity used upon exposing the substrate, and
the other of the first and second sets of processing conditions is a focus state of the projection optical system upon exposing the substrate.

5. The evaluation device according to claim 1, wherein
the detection unit detects a polarized component of the illumination light reflected by the processed surface of the substrate, and
at least one of the polarization state and an angle of incidence of the illumination light incident on the substrate differs among the plurality of sets of evaluation conditions.

6. An exposure system comprising:
an exposure unit including a projection optical system that exposes a surface of a substrate with a pattern; and
the evaluation device described in claim 1;
processing conditions in the exposure unit being corrected on the basis of the first set of processing conditions estimated by the estimating unit of the evaluation device.

7. The evaluation device according to claim 1, further comprising:
an evaluation condition setting unit that selects the plurality of sets of evaluation conditions based on a change in a detection result of the diffracted light beams obtained by the detection unit with respect to a change in the first or second sets of the processing conditions obtained under a plurality of sets of the evaluation conditions.

8. The evaluation device according to claim 1, further comprising:
a calculating unit configured to output a calculation result for estimating the first set of processing conditions and the second set of processing conditions at the time of processing the substrate by detection results of the detection unit based on the plurality of sets of evaluation conditions,
wherein the estimating unit estimates the at least one of the first set of processing conditions and the second set of processing conditions at the time of processing the substrate, on the basis of the calculation result of the calculating unit.

9. The evaluation device according to claim 1, wherein
the structure on the substrate is a structure for an actual device, and
the detection unit detects the diffracted light beams coming from the structure for the actual device on the substrate.

10. An evaluation method comprising the steps of:
illuminating, using an illumination unit with illumination light, a substrate having a structure formed with a plurality of sets of processing conditions including first and second sets of processing conditions;
detecting, using a detection unit, diffracted light beams coming from a processed surface of the substrate due to the illumination light;
estimating at least one of the first set of processing conditions and the second set of processing conditions at the time of processing the substrate, based on a detection result of the diffracted light beams obtained by detecting light coming from the processed surface under a plurality of sets of evaluation conditions among which diffraction conditions differ; and
controlling, using a controller, a relative movement between a stage on which the substrate is mountable and one of the illumination unit and the detection unit, such that the detection unit detects the diffracted light beams under the plurality of sets of evaluation conditions among which diffraction conditions differ.

11. The evaluation method according to claim 10, wherein
the plurality of sets of evaluation conditions include first and second sets of evaluation conditions; and
the step of estimating estimates at least one of the first set of processing conditions and the second set of processing conditions on the basis of a difference between the detection result obtained under the first set of evaluation conditions and the detection result obtained under the second set of evaluation conditions upon performing the estimation.

12. The evaluation method according to claim 9, wherein
the difference is a difference after carrying out at least one of a process of adding an offset and a process of applying any magnification to at least one detection value in the detection result obtained under the first set of evaluation conditions and the detection result obtained under the second evaluation conditions.

13. The evaluation method according to claim 10, wherein
processing the substrate includes exposing the substrate through a projection optical system;
one of the first and second sets of processing conditions is an exposure quantity used upon exposing the substrate; and
the other of the first and second sets of processing conditions is a focus state of the projection optical system upon exposing the substrate.

14. The evaluation method according to claim 10, wherein
upon the light coming from the processed surface of the substrate being detected, a polarized component of the illumination light reflected by the processed surface is detected, and
at least one of the polarization state and an angle of incidence of the illumination light incident on the substrate differs among the plurality of sets of evaluation conditions.

15. The evaluation method according to claim 10, wherein
the structure is provided in a plurality of regions of a processed surface of an evaluation substrate by processing the evaluation substrate while changing at least one of the first and second sets of processing conditions,
the processed surface of the evaluation substrate is illuminated with the illumination light,
light coming from the processed surface of the evaluation substrate due to the illumination light is detected, and
using a plurality of detection results obtained by detecting the light coming from the processed surface of the evaluation substrate under a plurality of conditions in which at least one of illumination conditions of the illumination light and detection conditions for the light coming from the processed surface of the evaluation substrate differs, the plurality of sets of evaluation conditions that produce a detection result being capable of suppressing an amount of change relative to a change in the second set of processing conditions is found in advance and stored.

16. The evaluation method according to claim 15, wherein upon the plurality of sets of evaluation conditions being found in advance and stored, an arithmetic expression applied in order to suppress the amount of change relative to a change in the second set of processing conditions is found and stored in a detection result obtained by detecting the light coming from the processed surface of the substrate under the plurality of sets of evaluation conditions.

17. A processing method comprising the steps of:
providing a pattern by processing a surface of a substrate;
estimating the first set of processing conditions of the substrate using the evaluation method described in claim 10; and
correcting processing conditions used upon exposing the substrate on the basis of the first set of processing conditions estimated in the evaluation method.

18. A device manufacturing method having a step of processing for providing a pattern in a surface of a substrate, the method comprising the step of:
performing the step of processing using the processing method described in claim 17.

19. A device manufacturing method having a step of processing for providing a pattern in a surface of a substrate, the method comprising the steps of:
performing the step of processing using the processing method described in claim 17; and
storing an arithmetic expression applied in order to suppress an amount of change relative to a change in the second set of processing conditions in accordance with the device to be manufactured.

20. The evaluation method according to claim 10, further comprising:
generating a calculation result for estimating the first set of processing conditions and the second set of processing conditions at the time of processing the substrate by detection results based on the plurality of sets of evaluation conditions,
wherein the at least one of the first set of processing conditions and the second set of processing conditions at the time of processing the substrate is estimated on the basis of the calculation result generated.

21. The evaluation method according to claim 10, wherein
the structure on the substrate is a structure for an actual device, and
the detection unit detects the diffracted light beams coming from the structure for the actual device on the substrate.

* * * * *

UNITED STATES PATENT AND TRADEMARK OFFICE
CERTIFICATE OF CORRECTION

PATENT NO. : 10,274,835 B2
APPLICATION NO. : 14/654394
DATED : April 30, 2019
INVENTOR(S) : Kazuhiko Fukazawa Page 1 of 1

It is certified that error appears in the above-identified patent and that said Letters Patent is hereby corrected as shown below:

In the Claims

Claim 12, Column 28, Line 27, "claim 9" should read as -- claim 11 --.

Signed and Sealed this
Twenty-second Day of October, 2019

Andrei Iancu
*Director of the United States Patent and Trademark Office*